(12) United States Patent
Nicholson et al.

(10) Patent No.: US 11,447,455 B2
(45) Date of Patent: Sep. 20, 2022

(54) POLYMORPHS OF HERBICIDAL SULFONAMIDES

(71) Applicant: FMC Corporation, Philadelphia, PA (US)

(72) Inventors: Paul Nicholson, Ewing, NJ (US); Karl Kauffman, Sykesville, MD (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 16/470,777

(22) PCT Filed: Dec. 14, 2017

(86) PCT No.: PCT/US2017/066309
§ 371 (c)(1),
(2) Date: Jun. 18, 2019

(87) PCT Pub. No.: WO2018/118621
PCT Pub. Date: Jun. 28, 2018

(65) Prior Publication Data
US 2019/0337905 A1 Nov. 7, 2019

Related U.S. Application Data

(60) Provisional application No. 62/436,519, filed on Dec. 20, 2016.

(51) Int. Cl.
*C07D 249/12* (2006.01)
*A01N 43/653* (2006.01)

(52) U.S. Cl.
CPC ......... *C07D 249/12* (2013.01); *A01N 43/653* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 4,818,275 | A | 4/1989 | Theodoridis |
| 5,990,315 | A | 11/1999 | Dumas |
| 6,713,433 | B2 | 3/2004 | Jimoh |
| 7,169,952 | B2 | 1/2007 | Smeltz et al. |
| 8,133,846 | B2 | 3/2012 | Dominiani, Jr. et al. |
| 9,440,932 | B2 | 9/2016 | Framroze |
| 2003/0004063 | A1 | 1/2003 | Jimoh |
| 2015/0005166 | A1 | 1/2015 | Jones et al. |

FOREIGN PATENT DOCUMENTS

| | | |
|---|---|---|
| WO | 2015/168010 | 11/2015 |
| WO | 2016/003997 | 1/2016 |
| WO | 2016/033285 | 3/2016 |

OTHER PUBLICATIONS

PubMed Compound Summary for CID 86369, 'Sulfentrazone', U.S. National Library of Medicine, Jun. 24, 2005 (Jun. 24, 2005), p. 1-8 (https://pubchem.ncbi.nlm.nih.gov/compound/86369); p. 8.
Mirmehrabi et al. 'An approach to solvent screening for crystallization of polymorphic pharmaceuticals and fine chemicals', Journal of Pharmaceutical Sciences, May 31, 2005 (May 31, 2005), vol. 94, pp. 1560-1576; p. 1560, p. 1561.
University of California Irvine Crystallization, Jun. 4, 2012 (Jun. 4, 2012), p. 1-3 (http://faculty.sites.uci.edu/chem11/files/2013/11/RDGcrystallization.pdf); p. 2.
PerkinElmer 'Differential Scanning Calorimetry (DSC)', PerkinElmer, 2013-2014, p. 1-9 (https://www.perkinelmer.com/CMSResources/Images/44-74542GDE_DSCBeginnersGuide.pdf); p. 4, p. 5, p. 8.
International Search Report of copending PCT/US17/66309 patent application dated Mar. 6, 2018.
Liu, Changjling, World Pesticide Information Book, Edition 1, p. 133-135, Chemical Industry Press, Published Mar. 31, 2000.
Harry G. Brittain, Center for Pharmaceutical Physics, Milford, New Jersey, USA, Drugs and the Pharmaceutical Sciences, Second Edition, "Polymorphism in Pharmaceutical Solids" 2009.
EPA, United States Environmental Protection Agency, "Pesticides Fact Sheet for Sulfentrazone" 1997.
Balbach, S. and Korn, C., "Pharmaceutical evaluation of early development candidates 'the 100 mg-approach'", International Journal of Pharmaceutics, 2004, vol. 275, pp. 1-12.
Singhal, D. and Curatolo, W., "Drug polymorphism and dosage form design: a practical perspective", Advanced Drug Delivery Reviews, 2004, vol. 56, pp. 335-347.
Caira, Mino R., "Crystalline Polymorphism of Organic Compounds", Design of Organic Solids, pp. 163-208, 1998.

*Primary Examiner* — Alton N Pryor
(74) *Attorney, Agent, or Firm* — FMC Corporation; Kevin S. Dobson

(57) ABSTRACT

Solid polymorphic forms of sulfentrazone are described. Particularly, a new polymorphic form of sulfentrazone is described herein as sulfentrazone-1, having surprising property advantages over technical sulfentrazone. Processes for the preparation of sulfentrazone-1, herbicidal compositions comprising sulfentrazone-1, and methods of its use are described.

15 Claims, 8 Drawing Sheets

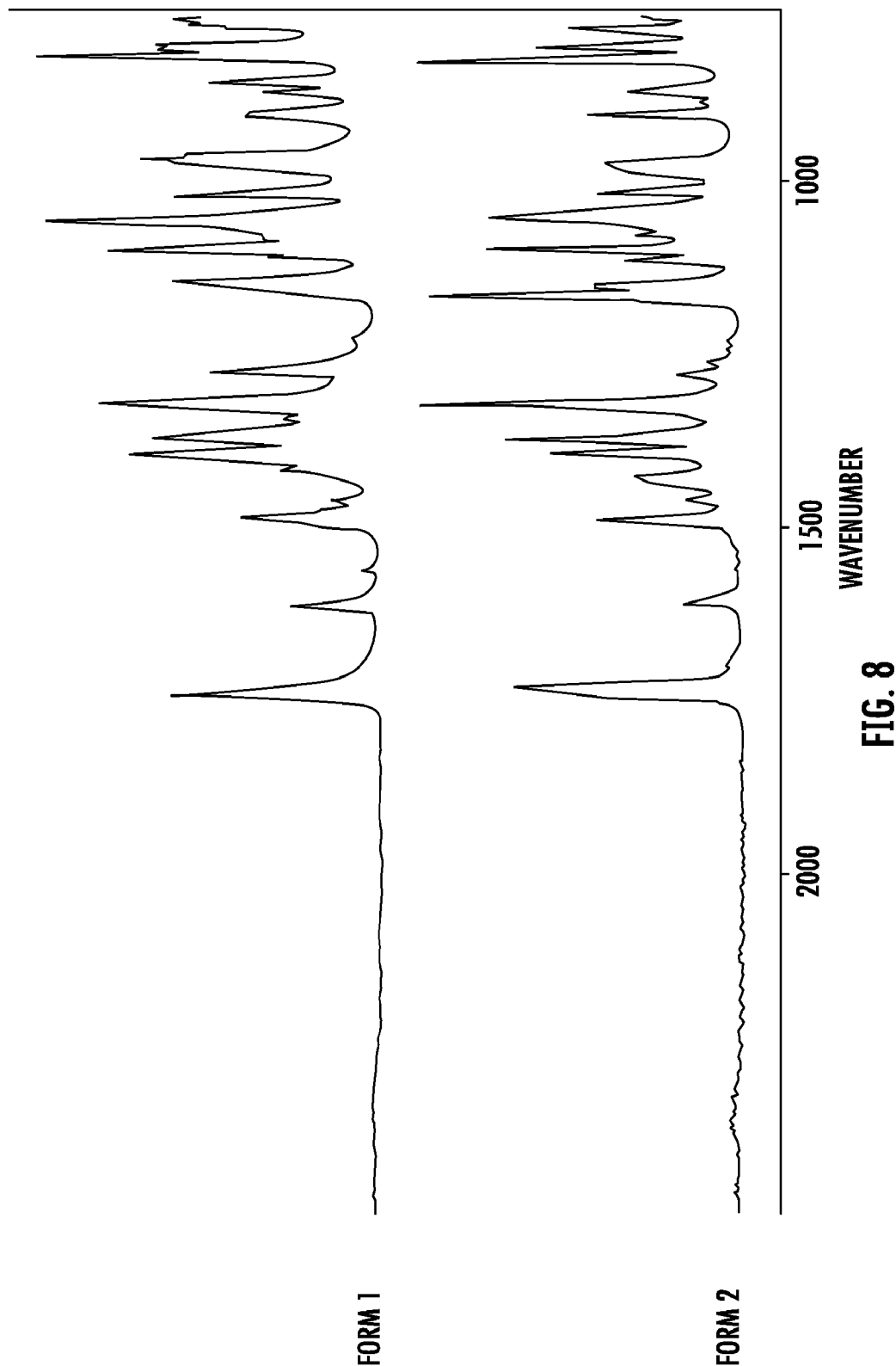

POLYMORPHS OF HERBICIDAL SULFONAMIDES

FIELD OF THE INVENTION

This invention relates to a new solid polymorphic form of an N-(substituted phenyl)sulfonamide, to processes for its preparation, compositions comprising the solid form and methods of its use in herbicides.

BACKGROUND OF THE INVENTION

It is known in the art that some N-(substituted phenyl) sulfonamides may be pesticidally active and that such compounds are useful in the preparation of certain pesticides. For example, the use of N-[2,4-dichloro-5-[4-(difluoromethyl)-4,5-dihydro-3-methyl-5-oxo-1H-1,2,4-triazol-1-yl] phenyl]methanesulfonamide as an herbicide—depicted below as formula I and commonly known as sulfentrazone—is disclosed in U.S. Pat. No. 4,818,275. Processes for the preparation of sulfentrazone are disclosed in U.S. Pat. Nos. 4,818,275 and 7,169,952. Commercial products incorporating sulfentrazone have been prepared using technical grade material that comprise a mixture of polymorphic forms of sulfentrazone. Technical grade sulfentrazone material can typically include entrapped solvent, such as toluene, as an impurity from the processes to prepare it. Entrapped solvents present in technical grade sulfentrazone can present problems with exposure during subsequent processing and/ or use of technical grade sulfentrazone.

It can be desirable to reduce volatile emissions of solvent during milling operations with technical grade sulfentrazone.

SUMMARY OF THE INVENTION

It has now been found that a new crystalline polymorphic form of sulfentrazone can be obtained in high purity, having substantially reduced content of entrapped solvent. Surprisingly, it has been found that the new crystalline form of sulfentrazone has advantages as an herbicide over conventional (technical grade) sulfentrazone, and at the same time does not have some of the disadvantages of technical grade sulfentrazone, which typically contains solvent that is entrapped in the partially amorphous solid form of the technical grade material.

Accordingly, this invention relates to sulfentrazone, depicted below as formula I, obtained as a novel crystalline form, and its more effective use as an herbicide.

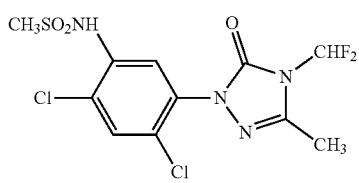

I

In one aspect of the present application, there is provided a crystalline polymorph of the compound of formula I, N-[2,4-dichloro-5-[4-(difluoromethyl)-4,5-dihydro-3-methyl-5-oxo-1H-1,2,4-triazol-1-yl]phenyl]methanesulfonamide, alternatively referred to herein as "crystalline sulfentrazone" or more particularly as "sulfentrazone-1".

In another aspect, the present application provides a process for preparing sulfentrazone-1, said process comprising the step of crystallizing sulfentrazone-1 from a solution comprising, substantially: (i) a polymorphic form of sulfentrazone that is substantially different from the crystalline form of sulfentrazone-1 and (ii) a polar, protic solvent selected from the group consisting of $C_{1-4}$ alcohols, water and combinations thereof.

In another aspect, the present application describes a crystalline polymorphic form of the compound of formula I, N-[2,4-dichloro-5-[4-(difluoromethyl)-4,5-dihydro-3-methyl-5-oxo-1H-1,2,4-triazol-1-yl]phenyl]methanesulfonamide (sulfentrazone-1) obtained by a process comprising the step of crystallizing sulfentrazone-1 from a solution comprising, substantially: (i) a polymorphic form of sulfentrazone that is substantially different from the crystalline form of sulfentrazone-1 and (ii) a polar, protic solvent selected from the group consisting of $C_{1-4}$ alcohols, water and combinations thereof.

The process may further comprise heating a slurry of toluene-containing N-[2,4-dichloro-5-[4-(difluoromethyl)-4,5-dihydro-3-methyl-5-oxo-1H-1,2,4-triazol-1-yl]phenyl] methanesulfonamide in a polar, protic solvent selected from the group consisting of $C_{1-4}$ alcohols, water and combinations thereof to provide a melt; and removing the toluene by azeotropic co-distillation prior to precipitating sulfentrazone-1.

In still another aspect, the present application provides an herbicidal composition comprising an herbicidally effective amount of N-[2,4-dichloro-5-[4-(difluoromethyl)-4,5-dihydro-3-methyl-5-oxo-1H-1,2,4-triazol-1-yl]phenyl]methanesulfonamide comprising sulfentrazone-1 in admixture with a suitable carrier.

In another aspect, the invention also provides a method of controlling undesired plant growth, the method comprising applying an herbicidally effective amount of sulfentrazone-1 to the locus where control is desired.

BRIEF DESCRIPTION OF THE DRAWINGS

FIG. 8 shows the fingerprint region of the FTIR spectrum of sulfentrazone-1 overlaid with a vertical offset over the fingerprint region of the FTIR spectrum of technical sulfentrazone.

DETAILED DESCRIPTION OF THE INVENTION

Figure 1:
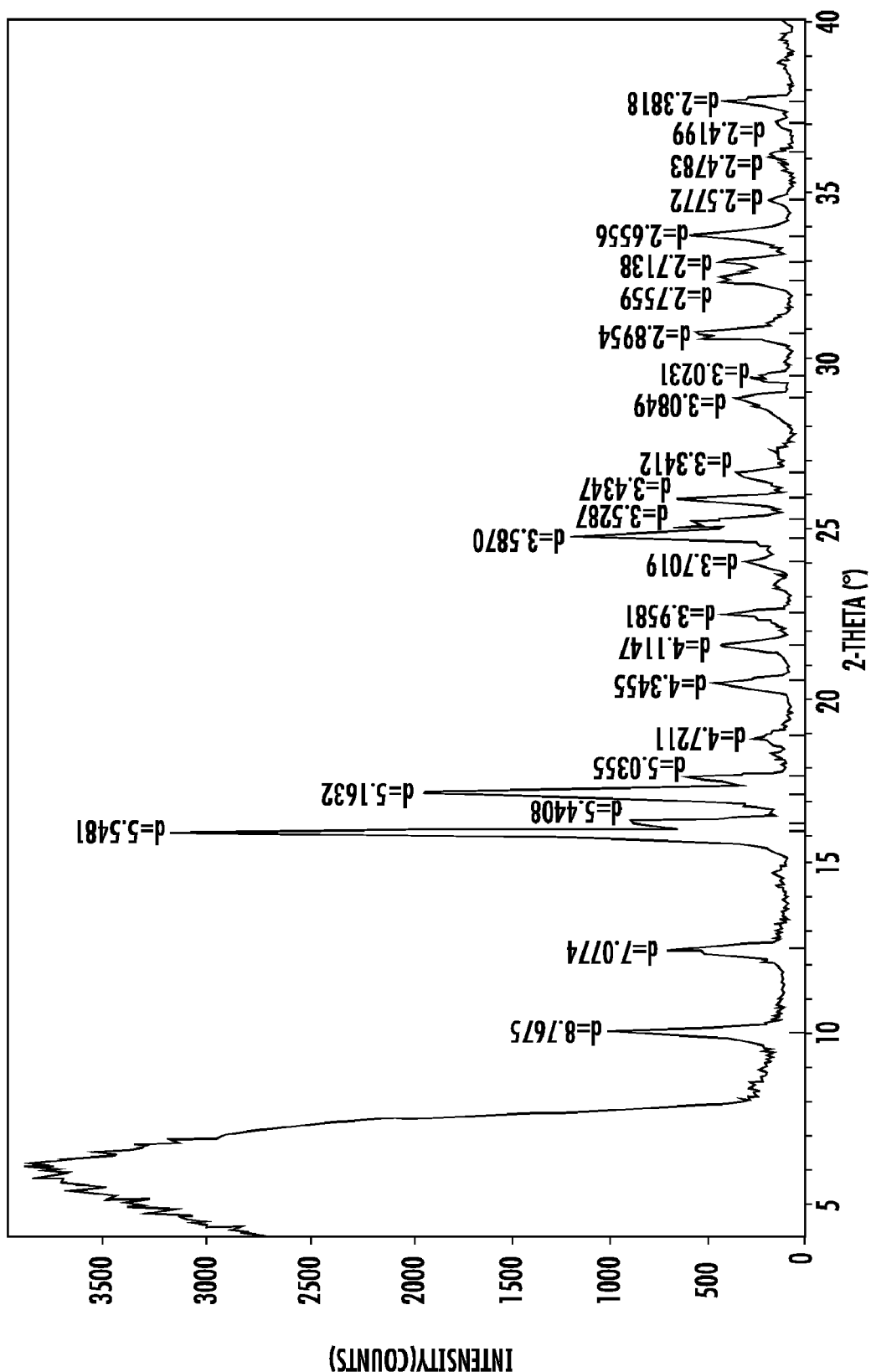
FIG. 1 shows the powder X-ray diffraction pattern of sulfentrazone-1.

In one embodiment, the present invention comprises a stable polymorphic crystalline form of sulfentrazone (sulfentrazone-1), characterized by the properties further described hereinbelow.

The term "sulfentrazone" is a common name for N-[2,4-dichloro-5[4-(difluoromethyl)-4,5-dihydro-3-methyl-5-oxo-1H-1,2,4-triazol-1-yl]phenyl]methanesulfonamide. As used herein, "sulfentrazone" can generically refer to any polymorphic form of N-[2,4-dichloro-5-[4-(difluoromethyl)-4,5-dihydro-3-methyl-5-oxo-1H-1,2,4-triazol-1-yl]phenyl] methanesulfonamide or to all polymorphic forms, or to combinations thereof. It is understood, however, that for the purposes of this invention any reference to "sulfentrazone-1" is reference to the new crystalline form of sulfentrazone as described by the present application. "Polymorph Form 2", "Form 2", or similar terms can be used herein to refer to the polymorphic form of formula I substantially present in technical grade sulfentrazone (alternatively, "technical sulfentrazone").

Polymorphism is known and understood by those of ordinary skill in the chemical arts to be the property of certain, substantially crystalline, compounds that exist in different 3-dimensional spatial arrangements. It is known that different polymorphic forms can potentially take on different physical properties attributable to the various spatial arrangements of the different forms of the polymorphic compounds. The different properties of the compound that can be affected can include: crystal shape, density, hardness, color, chemical reactivity, melting point, hydroscopic nature, affinity for solvent, solubility, behavior in complex mixtures, dissolution rate and biological availability, for example. Whether such different forms will have different properties cannot be readily predicted by one of ordinary skill, however. It is also not predictable by one of ordinary skill how and to what extent such differences can affect the properties exhibited by different polymorphic forms.

Polymorphic compounds are not isomeric compounds. Isomers are chemically different compounds wherein covalent bonding between the atoms of the molecules are unique to each isomer; isomers cannot be interconverted to their isomeric forms without making and breaking covalent bonds. Such is not the case with polymorphic forms of a crystalline compound, which forms can be interconverted or otherwise modified by physical means, that is, without making or breaking covalent bonds. Therefore, some polymorphic forms can be susceptible to changes in conditions that affect their 3-dimensional shape and, therefore, can be relatively more or less stable forms. Differences in stability of certain polymorphic forms can affect the reliability and/or the effectiveness of certain polymorphic forms in a particular use or application.

In the context of this invention, it has now been discovered that sulfentrazone can exist in more than one crystalline form in the solid state and is, therefore, polymorphic. Generally, a crystalline form of a compound contains orderly repeating patterns of the molecules extending in all three spatial dimensions. Highly ordered spatial arrangements tend to increase the degree of crystallinity. In contrast, an amorphous solid form has no long-range order in the spatial arrangement of the molecules. It can be possible that different polymorphic forms of a crystalline compound have both crystalline and amorphous regions. The degree of crystallinity of a compound can depend on the balance or interaction between crystalline regions and amorphous regions of the polymorphic compound.

Sulfentrazone is a biologically active compound—an herbicide. Surprisingly it has been found in the present invention that the difference in crystal structures between sulfentrazone-1 and technical grade sulfentrazone, which has a different polymorphic form, can provide an herbicide having different biological properties from other polymorphic forms of sulfentrazone.

In one embodiment of the present invention, advantage can be taken of the discovery that different polymorphic forms of sulfentrazone are more herbicidally effective than other polymorphic forms. For example, the development of production methods, formulations, and the quality and efficacy of plant treatment agents, such as herbicides, can be affected by manufacture and use of different polymorphic forms of sulfentrazone.

Particularly, it has been found that sulfentrazone-1 can be more herbicidally effective than technical sulfentrazone. Sulfentrazone-1 can demonstrate extended efficacy compared with technical sulfentrazone. Sulfentrazone-1 can be effective at lower rates of application than technical sulfentrazone.

Conventional practice provides that technical grade sulfentrazone can be obtained according to the process described in U.S. Pat. No. 7,169,952. Technical sulfentrazone finds use as an effective herbicide to control certain weeds. Precipitation of solid technical material from a toluene solution of sulfentrazone can be conducted as described therein. Conventional practice in the production of sulfentrazone typically results in solvent being entrapped in the solid sulfentrazone material obtained. For example, the technical sulfentrazone used, characterized and described herein contains about 4.8 to 5.0 weight % of toluene entrapped in the solid technical material, based on the total weight of the technical material. Notably, sulfentrazone-1 of the present invention is substantially free of toluene or other aromatic solvents; that is, sulfentrazone-1 comprises less than about 4.5 weight % toluene, based on the total weight of the sulfentrazone composition. In preferred embodiments of the present invention, sulfentrazone-1 comprises less than about 2 weight %, or less than about 1 weight %, or less than about 0.5 weight %, or less than about 0.2 weight % toluene or other solvents, particularly organic solvents and/or aromatic solvents, wherein the percentage is based on the total weight of sulfentrazone composition.

Specifically, it has been found that sulfentrazone-1 is a stable polymorph of sulfentrazone, and will not readily convert to other forms of sulfentrazone upon changed conditions, such as further loss of solvent from the crystal structure of sulfentrazone-1.

Use of sulfentrazone-1 as an herbicide can be advantageous due to its stability and the absence of entrapped aromatic solvent such as toluene and therefore herbicidal compositions comprising sulfentrazone-1 can be preferred, such as granular sulfentrazone consisting essentially of sulfentrazone-1, or in herbicidal mixtures of sulfentrazone with at least one agriculturally acceptable carrier or diluent, wherein the sulfentrazone comprises or consists essentially of sulfentrazone-1.

Sulfentrazone-1 can be obtained in an isolated solid form that is essentially free from solvents, other polymorphic forms of sulfentrazone, or other components that may affect the basic and novel characteristic properties of sulfentrazone-1. Such basic and novel characteristics of sulfentrazone-1 include: physical properties such as crystallinity and melting behavior; stability against conversion to other polymorphic forms of sulfentrazone; and increased efficacy as an herbicide, for example.

Assaying the solid phase for the presence of crystals may be carried out by conventional methods known in the art. For example, it is convenient and routine to use powder X-ray diffraction techniques. Other techniques that may be used include differential scanning calorimetry (DSC), thermogravimetric analysis (TGA) and Raman or Infra-red spectroscopy such as Fourier Transform Infra-red spectroscopy (FTIR), NMR, gas chromatography or HPLC. Single crystal X-ray diffraction can be especially useful in identifying crystal structures.

When describing the 2-theta-reflections in X-ray diffraction patterns, it is understood that ±0.2° can also be expressed as "plus or minus 0.2 degrees 2-theta". It should be understood, however, that relative intensities and assignments of the peaks of polymorphic forms depicted in the figures can vary depending on several factors, including sample preparation, mounting, and the instrument and analytical procedure and settings used to obtain the spectrum. As such, the peak observed in the figures and assignments listed herein is intended to encompass variations that fall within plus or minus 0.2 degrees 2-theta. It should be noted that X-ray diffraction patterns described herein as characteristic of sulfentrazone-1 can include additional peaks that are not necessarily characteristic of sulfentrazone-1, or probative of the presence of a different polymorphic form of sulfentrazone. The same caveat can be applied to the DSC and FTIR spectra provided herein.

In some embodiments, the term "substantially as shown in" when referring to a powder X-ray diffraction pattern, digital scanning calorimetry trace or Fourier Transform Infrared spectrum means that a pattern that is not necessarily identical to those depicted herein, but that falls within the limits of experimental error or deviations, when considered by one of ordinary skill in the art, is encompassed.

This invention also relates to methods for the preparation of sulfentrazone-1. Sulfentrazone-1 can be obtained directly without converting from other polymorphic forms of sulfentrazone or, alternatively, sulfentrazone-1 can be obtained by conversion of other polymorphic forms of sulfentrazone to sulfentrazone-1.

In one embodiment, the production of the sulfentrazone-1 of the present invention can be effected by crystallization or recrystallization of sulfentrazone-1 from a solution of technical grade sulfentrazone dissolved in a suitable solvent. The terms "crystallization" and "recrystallization" have somewhat different meanings in the chemical art, wherein "recrystallization" is generally understood to be a process whereby a solid material is first dissolved in a medium and then recrystallized from that medium. "Crystallization", on the other hand, is more generic and does not necessarily require a first step of dissolving the solid material. As used herein, the term "crystallization" may be used to refer to the process to obtain sulfentrazone-1 whether the process is actually a recrystallization process, or whether starting from a melt, a suspension, a dispersion or a solution of sulfentrazone.

Suitable solvents for the crystallization of sulfentrazone-1 are polar, protic solvents selected from the group consisting of: $C_{1-4}$ alcohols such as methanol, ethanol, propanol, iso-propanol, 1-butanol, 2-butanol, iso-butanol, t-butanol; water; and combinations thereof. Notable embodiments include those wherein the polar, protic solvent comprises (1) isopropanol; or (2) ethanol; or (3) butanol; or (4) water; or (5) a combination of an alcohol, such as butanol, and water. In some embodiments, isopropanol can be preferred.

For this, in a first step (step (i)) a solution or dispersion of sulfentrazone in one of the aforesaid solvents is prepared, and then in a second step (step (ii)) crystallization of the sulfentrazone from the mixture of step (i) is initiated.

The concentration of sulfentrazone in the solution used for the crystallization depends on the nature of the solvent and the solution temperature, and can be in the range from about 100 g/l to about 800 g/l.

Preferably the sulfentrazone solution prepared for the crystallization of sulfentrazone-1 utilizes sulfentrazone of a purity of at least 85%, or at least 90%, or in at least 95%; that is, the content of impurities other than organic solvents is not more than 15 weight %, or not more than 10 weight %, or not more than 5 weight %, based on the sulfentrazone dissolved in the solvent.

It can be preferable that the solution used for the crystallization comprises less than about 10 weight %, or less than about 5 weight % of a solvent other than the primary solvent, based on the total quantity of solvent. In a particular embodiment, the solvent comprises less than about 4 weight % toluene.

Toluene entrapped in technical sulfentrazone may be removed by azeotropic co-distillation to levels less than 4 weight % of the solvent prior to crystallization or recrystallization. While it can be preferred to remove entrapped toluene prior to crystallization of sulfentrazone-1, removal of toluene to levels of less than about 4 weight % is, alone, not effective in providing the sulfentrazone-1 of the present invention because the sulfentrazone obtained in this manner is substantially amorphous—not sulfentrazone-1. To obtain sulfentrazone-1, the process may therefore optionally further comprise (a) heating a slurry of toluene-containing sulfentrazone in a polar, protic solvent selected from the group consisting of $C_{1-4}$ alcohols, water and combinations thereof to provide a hot melt of sulfentrazone; and (b) removing the toluene by azeotropic co-distillation prior to proceeding to crystallize sulfentrazone-1. It can be preferred to use water in step (a). In a preferred embodiment, the hot melt of sulfentrazone is separated from the aqueous phase after removal of toluene and added to isopropanol maintained at 85° C. and cooled to precipitate sulfentrazone-1.

The dissolution of sulfentrazone can be carried out by one of the following methods, for example: (1) Dissolution of the sulfentrazone, preferably in a form different from sulfentrazone-1, in one of the aforesaid polar, protic solvents, or (2) preparation of the sulfentrazone by a chemical reaction and transfer of the reaction mixture, if necessary after removal of reagents and/or side products, into a solvent suitable for crystallization according to the invention. As can be appreciated by one of ordinary skill, other methods can be used to obtain a solution, suspension or other dispersion of sulfentrazone in a suitable solvent, and the process described herein is not strictly contingent on the method for obtaining a suitable mixture of sulfentrazone.

Any known form of sulfentrazone can be used to prepare the solution of the sulfentrazone. Amorphous sulfentrazone or a mixture of different crystalline modifications or a mixture of amorphous and crystalline sulfentrazone can be used. Notably, technical sulfentrazone such as Form 2, which includes entrapped toluene, can be used.

The dissolution or dispersion of the sulfentrazone is usually effected at temperatures in the range from about 20° C. to about 160° C., or at a temperature above about 50° C., or a temperature in the range of from about 50° C. to 140° C.

In an alternative embodiment, the solution of the sulfentrazone can be prepared by transferring a reaction mixture that contains the sulfentrazone into a suitable polar, protic solvent. It can be required in this embodiment that reaction solvents, reagents and other components be removed prior to mixing the reaction mixture with the solvent.

Crystallization of sulfentrazone-1 can be effected by alternative means, but generally crystallization of sulfentrazone-1 is effected by modifying the solubility of sulfentrazone in a solvent. In one embodiment, the crystallization of sulfentrazone-1 can be effected by cooling the solution which contains the dissolved sulfentrazone. The crystallization of sulfentrazone-1 is preferably effected from a polar, protic solvent at temperatures at or below about 100° C., at temperatures at or below about 80° C., or alternatively at temperatures at or below about 60° C. Crystallization of sulfentrazone-1 is preferably effected under controlled conditions, that is, the conditions of the crystallization are chosen to achieve a slow crystallization rate. When crystallization is effected by cooling, preferably the cooling rate is less than 10° C./minute.

Alternatively, crystallization of sulfentrazone-1 can be achieved via addition of a solubility-decreasing solvent, such as for example by addition of a nonpolar organic solvent, to a solution of sulfentrazone in a primary solvent. Alternatively water, or a combination of nonpolar organic solvent and water, can be used to decrease the solubility of sulfentrazone in the primary solvent. Conditions are selected wherein the crystallization of sulfentrazone-1 is controlled and is preferably slow. In the present process, "slow" would be understood by one of ordinary skill to be a rate of crystallization that is effective for obtaining sulfentrazone-1 preferentially over other forms of sulfentrazone or an amorphous form of sulfentrazone. One of ordinary skill in the art would know how to modify the addition of the solubility-decreasing solvent in a manner that manipulates the rate of crystallization, and such modification would not present an unreasonable degree of experimentation to find acceptable or optimal conditions for crystallizing sulfentrazone-1.

Still alternatively, sulfentrazone-1 can be crystallized from a solution of sulfentrazone by concentration of the solution which contains the dissolved sulfentrazone. Sulfentrazone can be concentrated in the solution by controlled removal of solvent, for example, or by adding sulfentrazone to the solution up to the saturation point of sulfentrazone in the solvent, or by a combination of any of the aforesaid measures.

The crystallization of sulfentrazone-1 can be promoted or accelerated by seeding with seed crystals of sulfentrazone-1, for example by adding seed crystals of sulfentrazone-1 before or during the crystallization. If seed crystals are added during the crystallization, the quantity thereof is typically 0.001 to 10 weight %, often 0.005 to 5 weight %, 0.01 to 1 weight %, and especially 0.05 to 0.5 weight %, based on the dissolved sulfentrazone.

If the crystallization is performed in the presence of seed crystals of sulfentrazone-1, these are preferably only added at a temperature at which the saturation concentration of the sulfentrazone in the solvent in question has been reached, that is, at or below that temperature at which the dissolved quantity of sulfentrazone forms a saturated solution in the solvent in question.

The crystallization should be efficient and productive. The crystallization may be carried out until at least about 80 weight %, preferably at least about 90 weight %, more preferably at least about 95 weight %, of the dissolved sulfentrazone crystallizes out as sulfentrazone-1.

The isolation of the sulfentrazone-1 from the mother liquor can be effected by known and conventional techniques for the separation of solid components from liquids, for example by filtration, centrifugation or by decantation. The isolated solid can be washed with a solvent in which the sulfentrazone-1 is poorly soluble or, preferably, is insoluble. For example, the crystallized product can be washed with: the solubility-decreasing solvent used to carry out the crystallization (that is, the crystallization solvent); or with water; or with a mixture of the crystallization solvent and water. The washing can be done in one or more steps. In a preferred embodiment, washing with water can be used as the final washing step. The washing is typically carried out at temperatures at or below about 30° C., at or below about 25° C., or at or below about 20° C.

The sulfentrazone-1 obtained as described above can be dried or, alternatively, can be used further without drying. It can be advantageous to use the wet sulfentrazone-1 without subjecting it to a drying step before using it in subsequent processing.

By means of the crystallization as described herein, the polymorphic form of sulfentrazone obtained consists of at least about 80 weight %, or at least about 85 weight %, or at least about weight 90%, or at least about 95 weight %, or at least about 96 weight %, or at least about 97 weight %, or at least about 98 weight % or at least about 99 weight % sulfentrazone-1. Notably, in any embodiment of the present invention, sulfentrazone-1 is substantially free of toluene or other aromatic solvents; that is sulfentrazone-1 has less than about 2%, or less than about 1%, or less than about 0.5%, or less than about 0.2% entrapped solvent.

Representative processes for preparation of Sulfentrazone-1 are described below.

To obtain a solution or dispersion of sulfentrazone suitable for crystallization of sulfentrazone-1, technical sulfentrazone (Form 2) is charged to water at a 1:3 weight ratio with vigorous agitation. The slurry is transferred to a steam-jacketed, agitated pressure-rated vessel and heated. During heating, the solid in the slurry is melted, liberating the toluene from the sulfentrazone and initiating boiling of the vessel contents and the removal of toluene as a toluene-water azeotrope. The azeotrope condenses and is separated in a decanter. The water can be recycled to the pot and the toluene can be recycled to the last step of the sulfentrazone manufacturing process.

When toluene has been removed, as determined by both vapor temperature and no additional toluene leaving the decanter, agitation is stopped and the phases separate, the sulfentrazone separates as an oil phase on the bottom. The vessel containing the sulfentrazone mixture is kept at about 130° C. and about 25 psig to keep the sulfentrazone from freezing and the water from boiling.

The sulfentrazone oil phase is drained into another vessel, containing a sufficient charge of isopropyl alcohol (IPA) to create a 30 weight % solution of the sulfentrazone in IPA. The IPA may be recycled filtrate from the product centrifuges. The crystallization may be expected to leave some (as much as about 2%) sulfentrazone in the mother liquor, and the IPA charge can be adjusted to achieve about 30% sulfentrazone concentration in the batch transferred to the crystallizer. The water phase left in the stripping vessel may be recycled back to the toluene stripping operation.

The IPA-sulfentrazone mixture is heated to about 85° C. to ensure all sulfentrazone is in solution before transferring to the crystallization step. It may be necessary to maintain a slight pressure on this vessel to suppress boiling. Crystallization can be allowed to occur over at least about 4 hours as the batch is cooled from about 75° C. to about 20° C. Optionally, the crystallization can be facilitated by seeding with crystals of sulfentrazone-1.

The crystallized mixture is fed to a basket centrifuge to separate the IPA from the crystalline sulfentrazone-1. The IPA mother liquor may be recycled back to the crystallization step. The centrifuge cake is washed with water. The water wash is diverted to separate collection to avoid diluting the IPA recycle solvent.

The crystallized sulfentrazone product, sulfentrazone-1, has a melting point of about 122° C., which provides opportunity to use a variety of drying equipment to dry the sulfentrazone crystals.

Alternatively, following the removal of toluene the sulfentrazone melt is highly dispersed in a water phase with high shear agitation and a circulating shear pump. The mixture can be agitated and circulated at a cooler temperature for the dispersed amorphous solid particles to crystallize. Preferably seed crystals of sulfentrazone-1 are added to the water phase prior to the dispersion and/or during cooling of the sulfentrazone mixture. The crystallization from water can be conducted in the same vessel used for the toluene removal, or the sulfentrazone melt phase is alternatively transferred to a second vessel for dispersion into water, cooling and crystallization. Sulfentrazone-1 can be isolated by known and conventional methods such as centrifuging, and/or filtering, optionally followed by washing and drying the sulfentrazone-1 crystals.

Alternatively, in another embodiment, following toluene removal the sulfentrazone melt can be crystallized from an aqueous phase containing 10 weight % of butanol. In this embodiment, the crystallization can be conducted in the same vessel used for the toluene removal by adding sufficient butanol to solubilize the sulfentrazone hot melt and, if necessary, adding water to provide the desired butanol/water ratio followed by cooling. It can be optional to seed with sulfentrazone-1 crystals. Alternatively, the sulfentrazone hot melt is transferred to a second vessel charged with a sufficient amount of butanol/water mixture for the crystallization. Sulfentrazone-1 can be isolated by known and conventional methods such as centrifuging, and/or filtering, optionally followed by washing and drying the sulfentrazone-1 crystals.

In one embodiment, the processes described herein provide sulfentrazone-1 in higher purity than technical sulfentrazone by substantially reducing the amount of aromatic solvents such as toluene in the solid form of sulfentrazone. This can provide material that has less environmental impact and can be formulated for herbicidal use with improved properties compared to previous sulfentrazone formulations.

Figure 4:
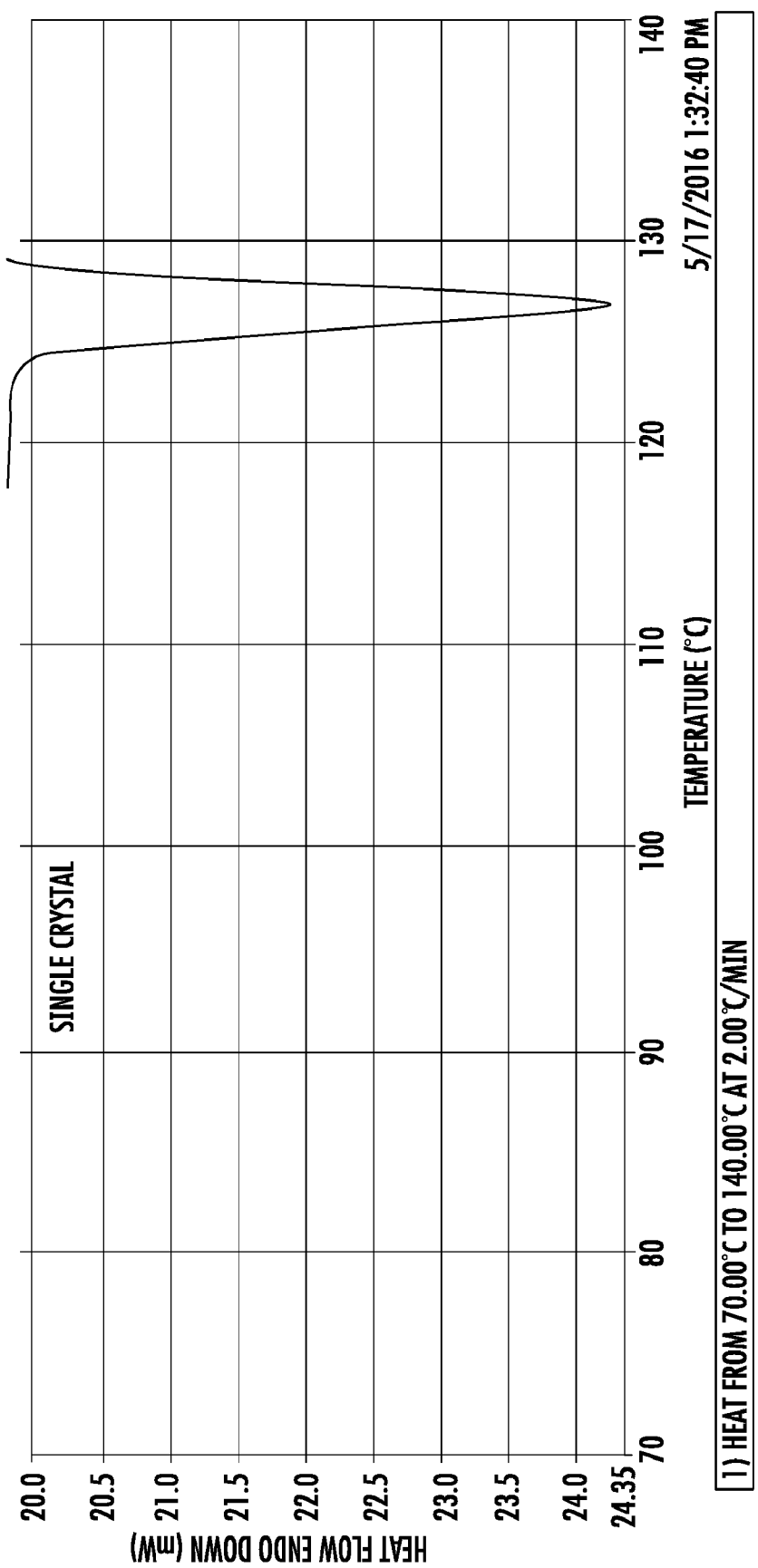
FIG. 4 shows the Differential Scanning calorimetry (DSC) trace of sulfentrazone-1.
Figure 5:
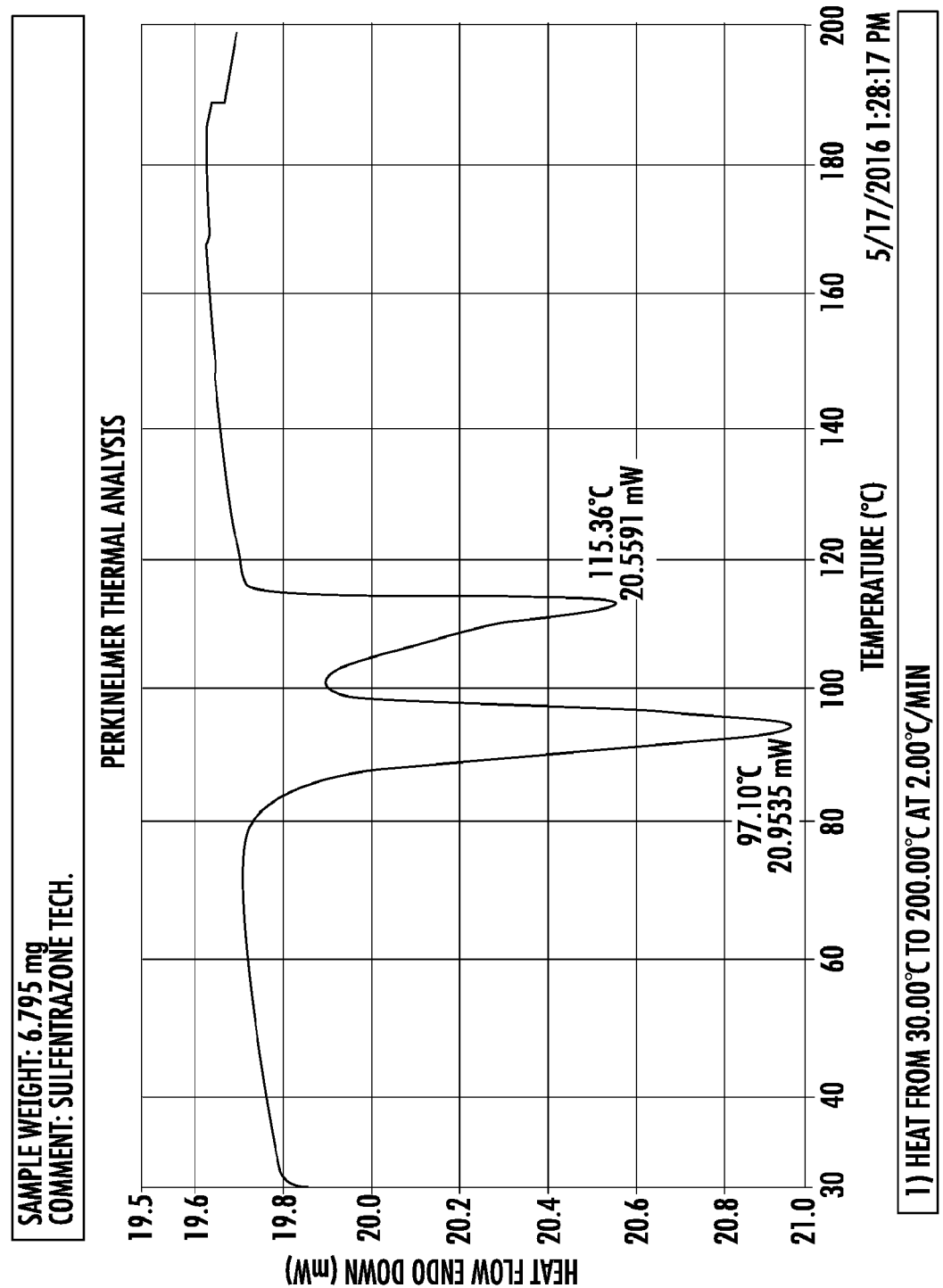
FIG. 5 shows the DSC trace of the polymorph of technical sulfentrazone.

Sulfentrazone-1 obtained as described herein can be characterized by differential scanning calorimetry (DSC) as having a melting range of from about 119° C. to about 130° C. Alternatively, or in addition, sulfentrazone-1 can be characterized as having an onset of melting in the range of from about 119° C. to about 125° C. Alternatively, or in addition, sulfentrazone-1 can be characterized as having an onset of melting at about 122° C. Alternatively, or in addition, sulfentrazone-1 can be characterized by a differential scanning calorimetry thermogram having a single endothermic peak at about 126±3° C., or in the range of from about 123° C. to about 129° C. In one embodiment sulfentrazone-1 can be characterized by a DSC thermogram substantially as shown in FIG. 4. By contrast, technical grade sulfentrazone (Form 2) can be characterized as having two broad endothermic peaks at about 97±10° C. and about 115±10° C. (FIG. 5).

Various other aspects and embodiments of the invention will now be illustrated in more detail by way of example and with reference to the figures.

FIG. 1 shows the powder X-ray diffraction pattern of sulfentrazone-1. The powder X-ray diffraction pattern shows peaks characteristic of sulfentrazone-1, including a peak, in terms of 2-theta, at about 15.9±0.2°, or comprising at least one peak, or one, two or three peaks in terms of 2-theta, of any of the peaks at about 15.9±0.2°, about 10.1±0.2°, or about 12.5±0.2°, or comprising at least one peak, or one, two, three, four or five peaks in terms of 2-theta, of any of the peaks at about 15.9±0.2°, about 10.1±0.2°, about 12.5±0.2°, about 33.7±0.2° or about 37.7±0.2°. Notably, the solid form of sulfentrazone-1 is characterized by having a powder X-ray diffraction pattern substantially as shown in FIG. 1.

Figure 2:
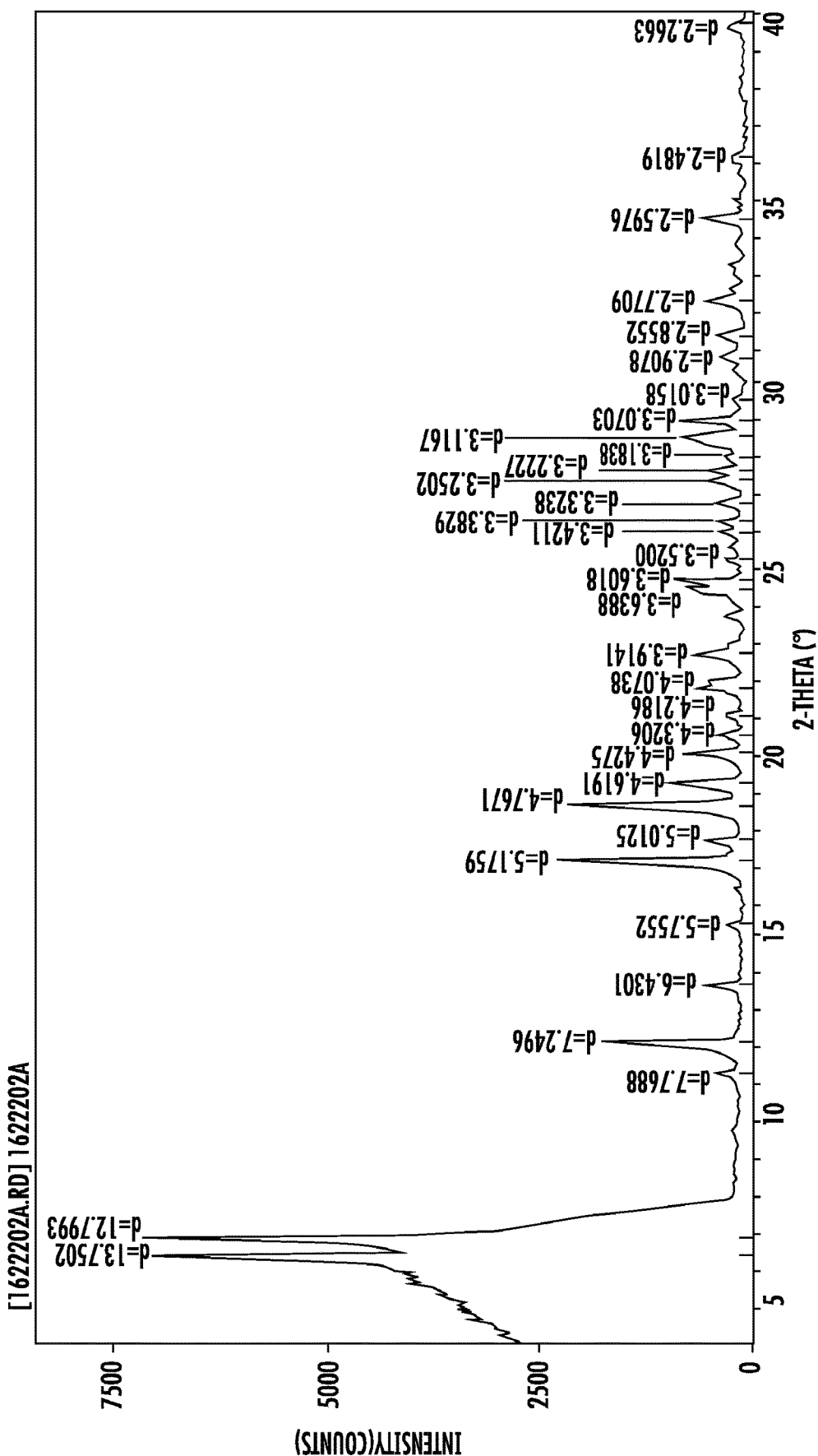
FIG. 2 shows the powder X-ray diffraction pattern of the polymorph of technical sulfentrazone (polymorphic form 2).

In contrast, as shown in FIG. 2, the powder X-ray diffraction pattern of the polymorph of technical sulfentrazone has none of the peaks identified above as characteristic of sulfentrazone-1. The powder X-ray diffraction pattern of Form 2 is characterized by a peak, in terms of 2-theta, at about 18.6±0.2°, or includes at least one peak, or one, two, three or four peaks in terms of 2-theta, of any of the peaks at about 12.2±0.2°, about 18.6±0.2°, about 19.2±0.2°, about 20.0±0.2°, or at least one peak, or one, two, three, four, five or six peaks in terms of 2-theta, of any of the peaks at about 12.2±0.2°, about 18.6±0.2°, about 19.2±0.2°, about 20.0±0.2°, about 29.1±0.2°, or about 34.5±0.2°.

Figure 3:
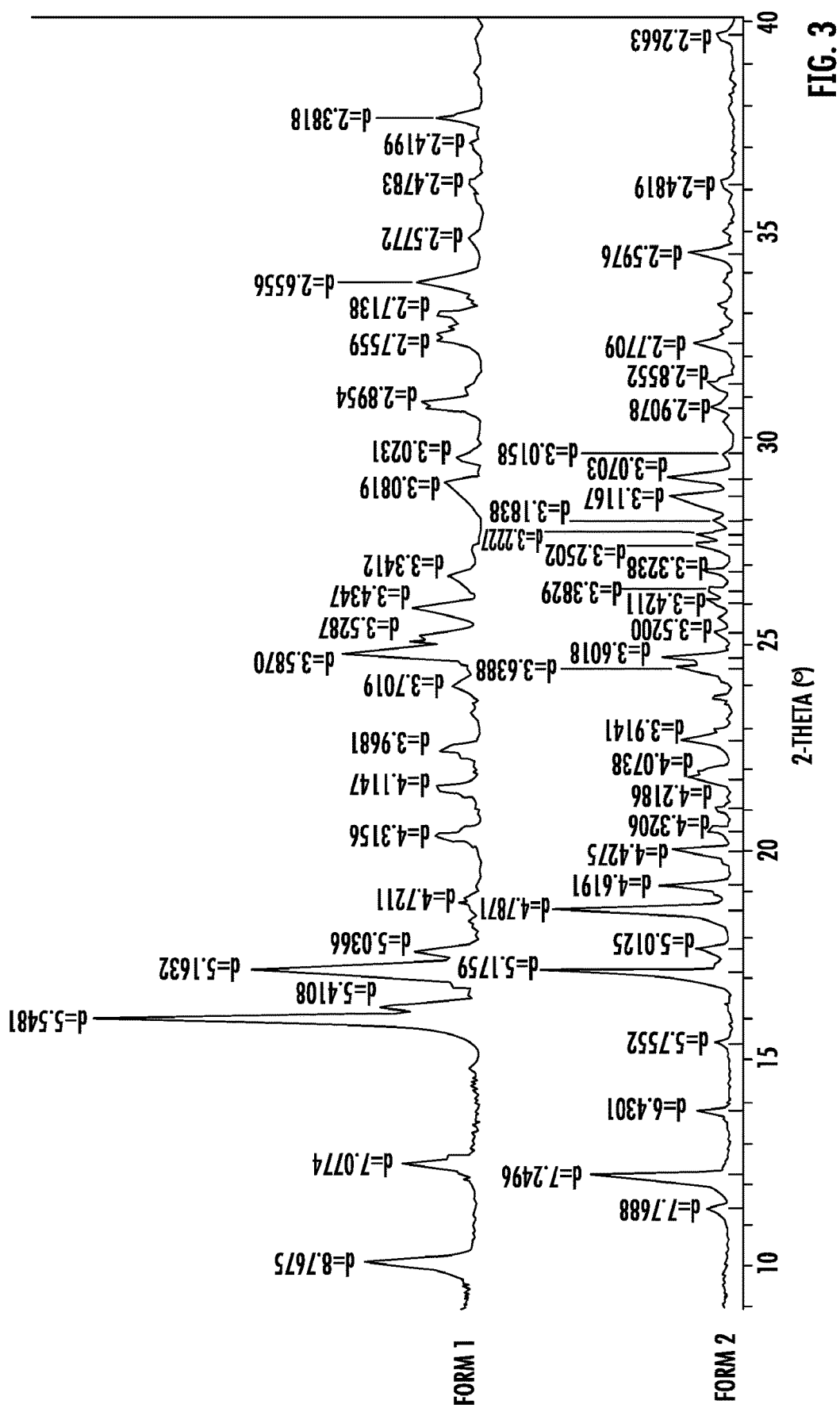
FIG. 3 shows the powder X-ray diffraction pattern of FIG. 1 overlaid with a vertical offset over the powder X-ray diffraction pattern of FIG. 2.

FIG. 3 shows the powder X-ray diffraction pattern of the polymorph of sulfentrazone named as sulfentrazone-1 overlaid with a vertical offset over the powder X-ray diffraction pattern of the polymorph of sulfentrazone named as Form 2, to illustrate the differences in the powder X-ray diffraction patterns of sulfentrazone-1 and Form 2. The differences between the X-ray diffraction patterns of sulfentrazone-1 and Form 2 are apparent in FIG. 3.

Sulfentrazone-1 can be characterized by its melting range, as observed during Differential Scanning calorimetry (DSC). FIG. 4 shows the DSC Trace of the polymorph of sulfentrazone-1 which is characterized by a single endothermic peak at about 126±3° C., with a melting point (onset of melting) at about 122±3° C.

FIG. 5 shows the DSC trace of the polymorph of technical sulfentrazone. It shows two broad endothermic peaks at about 97±10° C. and about 115±10° C. There is an absence of an endothermic peak at 126° C.

Figure 6:
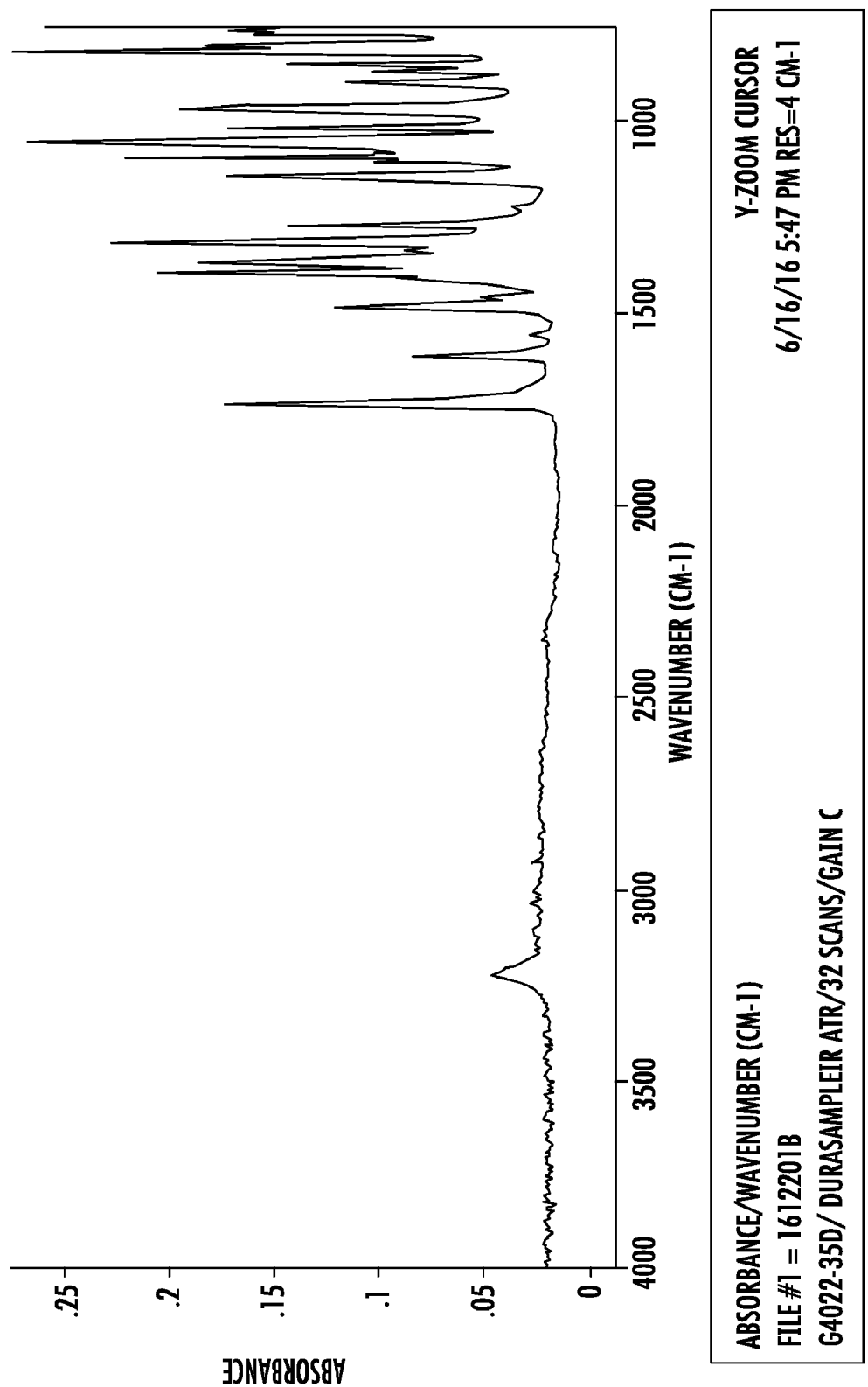
FIG. 6 shows the FTIR spectrum of sulfentrazone-1.

Sulfentrazone-1 may also be characterized by its FTIR spectrum. FIG. 6 shows the shows the FTIR spectrum of the polymorph of sulfentrazone-1. It is characterized by a Fourier Transform Infrared (FTIR) spectrum comprising a peak, in terms of wavenumber, at about $1273\pm2$ cm$^{-1}$, or comprising at least one peak, or one, two or three peaks in terms of wavenumbers, of any of the peaks at about $1614\pm2$ cm$^{-1}$, about $1273\pm2$ cm$^{-1}$, or about $854\pm2$ cm$^{-1}$, or comprising at least one peak, or one, two, three, four or five peaks in terms of wavenumbers, at about $1743\pm2$ cm$^{-1}$, about $1614\pm2$ cm$^{-1}$, about $1273\pm2$ cm$^{-1}$, about $1146\pm2$ cm$^{-1}$ or about $854\pm2$ cm$^{-1}$. Notably, the solid form of sulfentrazone-1 is characterized by a Fourier Transform Infrared (FTIR) spectrum substantially as shown in FIG. 6.

Figure 7:
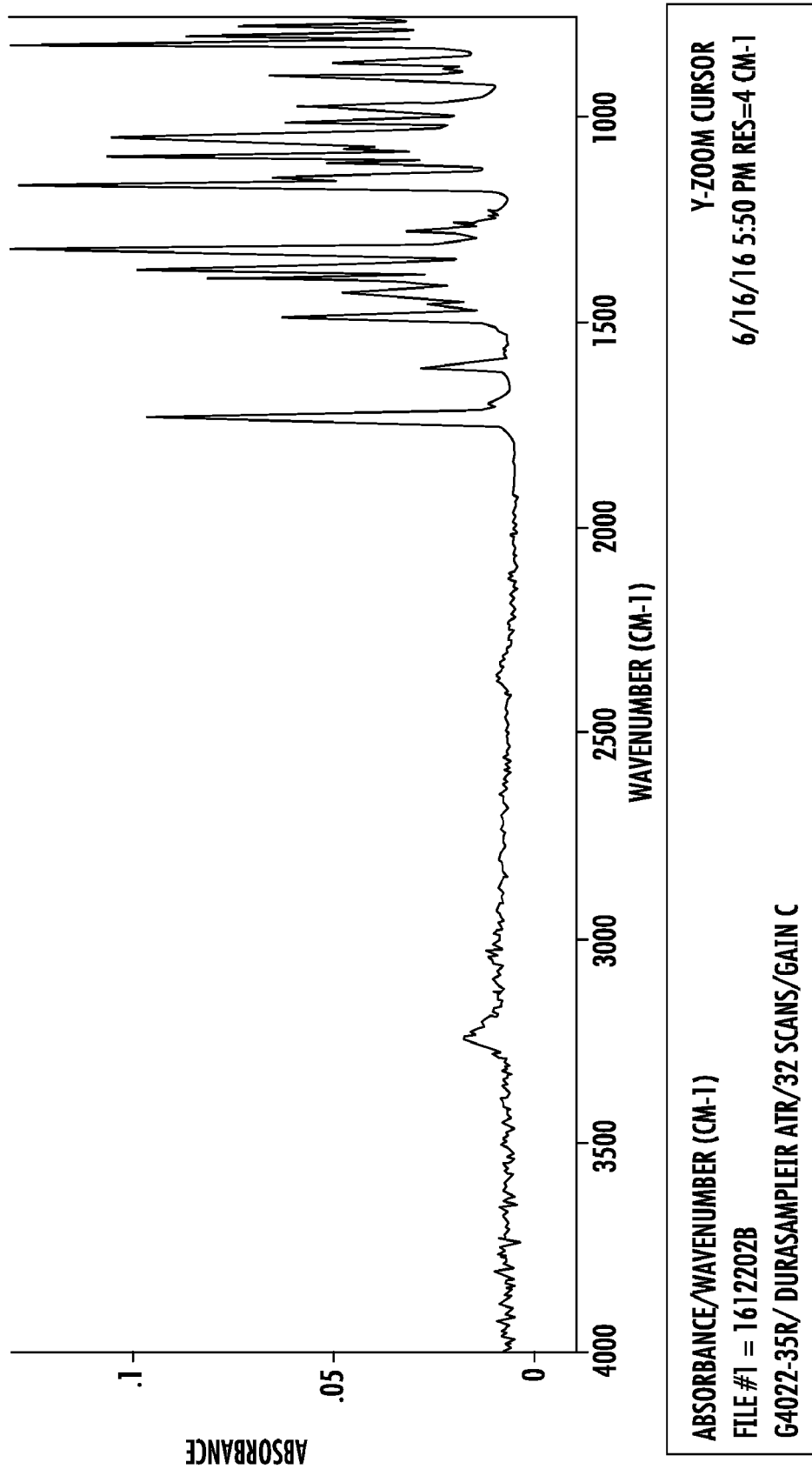
FIG. 7 shows the FTIR spectrum of the polymorph of technical sulfentrazone.

FIG. 7 shows the FTIR spectrum of the polymorph of sulfentrazone named as Form 2. There is a substantial absence of the characteristic peaks listed above for sulfenthrazone-1. Form 2 is characterized by a Fourier Transform Infrared (FTIR) spectrum comprising a peak, in terms of wavenumber, at about $1164\pm2$ cm$^{-1}$, or comprising at least one peak, or one, two or three peaks in terms of wavenumbers, of any of the peaks at about $1730\pm2$ cm$^{-1}$, about $1425\pm2$ cm$^{-1}$, or about $1164\pm2$ cm$^{-1}$.

FIG. 8 shows the fingerprint region of the FTIR spectrum of the polymorph of sulfentrazone named as sulfentrazone-1 overlaid with a vertical offset over the fingerprint region of the FTIR spectrum of the polymorph of sulfentrazone named as Form 2.

The sulfentrazone-1 polymorph of formula I may be applied in unchanged form but is more preferably incorporated into agrochemical compositions by conventional means. Accordingly, in a further aspect, the invention provides an agrochemical composition comprising the sulfentrazone-1 polymorph as defined above and at least one an agriculturally acceptable carrier or diluent.

In a still further aspect, this invention provides a method for combating or controlling weeds in crops of useful plants, which comprises treating the useful plants, seeds or cuttings thereof or the locus where control is desired with a composition comprising or consisting essentially of the sulfentrazone-1 polymorph of sulfentrazone.

Any method of application to weeds/crops of useful plants, or locus thereof, which is routinely used in agriculture may be used, for example application by spray or broadcast method typically after suitable dilution of the composition of the invention. The herbicidal efficacy of sulfentrazone-1 admixed with a suitable carrier or diluent can be determined generally according to methods described in U.S. Pat. No. 4,818,275, for example.

The term "plant" as used herein has its conventional meaning, and includes seedlings, bushes and trees.

The term "locus" as used herein includes not only areas where weeds may already be growing, but also areas where weeds have yet to emerge, and to areas under cultivation with respect to crops of useful plants. Areas under cultivation include land on which the crop plants are already growing and land intended for cultivation with such crop plants.

Crops of useful plants in which compositions of the invention may be used or the methods of the invention applied include perennial crops, such as citrus and coffee, and annual arable crops, such as for example soybeans, tobacco, sugarcane, mint, peanuts, sunflowers, pineapple and selected vegetables. Compositions and methods of the invention may also be used on turf, pasture, rangeland, rights of way etc. In particular they may be used on golf-courses, lawns, parks, sports-fields, race-courses and the like.

Plants suitable for use in the practice of the present invention include those which have been rendered tolerant to herbicides or classes of herbicides (e.g. ALS-, GS-, EPSPS-, PPO- and HPPD-inhibitors) by conventional methods of breeding or by genetic engineering. An example of a plant that has been rendered tolerant to imidazolinones, e.g. imazamox, by conventional methods of breeding is Clearfield® summer rape (canola). Examples of plants that have been rendered tolerant to herbicides by genetic engineering methods include e.g. glyphosate- and glufosinate-resistant maize varieties commercially available under the trade names RoundupReady® and LibertyLink®.

Plants suitable for use in the practice of the present invention also include those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate. Traits include those that increase plant defenses against insects, arachnids, nematodes and slugs and snails by virtue of toxins formed in the plants, in particular those formed in the plants by the genetic material from Bacillus thuringiensis (for example by the genes Cry1A(A1), Cry1A(b), Cry1A(c), Cry11A, Cry111A, CryIIIB2, Cry9c, Cry2Ab, Cry3Bb and Cry1F and also combinations thereof). Traits also include those that plant defenses against fungi, bacteria and viruses by systemic acquired resistance (SAR), systemin, phytoalexins, elicitors and resistance genes and correspondingly expressed proteins and toxins.

Plants suitable for use in the practice of the present invention also include those which are obtained by conventional methods of breeding or genetic engineering and contain so-called output traits (e.g. improved storage stability, higher nutritional value and improved flavor).

Plants and plant cultivars obtained by genetic engineering methods, if appropriate in combination with conventional methods, and parts thereof, may be treated by sulfentrazone-1 and compositions comprising it. Plant cultivars are understood as meaning plants having novel properties ("traits") which have been obtained by conventional breeding, by mutagenesis or by recombinant DNA techniques. These can be cultivars, bio- or genotypes. Depending on the plant species or plant cultivars, their location and growth conditions (soils, climate, vegetation period, diet), the treatment according to the invention may also result in superadditive "synergistic" effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected. The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further examples of such traits are a better defense of the plants against animal and microbial pests, such as against insects, mites, phytopathogenic fungi, bacteria and/or viruses, and increased tolerance of the plants to certain herbicidally active compounds. Examples of transgenic plants which may be mentioned are the important crop plants, such as soybeans, tobacco, and fruit plants (especially citrus fruits).

The term "weeds" as used herein means any undesired plant, and thus includes not only agronomically important weeds as described below, but also volunteer crop plants. The compositions comprising sulfentrazone-1 control broadleaf weeds such as lambsquarters, morningglories, nightshades, nutsedges and other sedges, pigweeds, waterhemp, pusley, euphorbia, commelina, spurge, anoda, beggarweed, carpetweed, cocklebur, copperleaf, croton, daisy, dayflower, galinsoga, groundcherries, jimsonweed, mexicanweed, mustards, poorjoe, purslane, starbur, and velvetleaf and grasses such as broadleaf signalgrass, goosegrass, barnyardgrass, crabgrasses, crowfootgrass, foxtail, johnsongrass, orchardgrass, and panicum.

The compositions according to the invention are suitable for pre-emergent application, total vegetation control and no-till cropping. Depending on the intended use, sulfentrazone-1 may be applied by itself or together with another herbicide before or after emergence of the plants. Treatment of the plants by simultaneous application of sulfentrazone-1 and another herbicide (for example, as a tank mix) may be preferred. The application rate of the herbicidal sulfentrazone-1 to be applied largely depends on the method of use. For field treatment, 0.001 to 5.0 kg of the polymorph/ha, preferably between 0.001 to 2 kg of the polymorph/ha, or preferably 0.005 to 1 kg/ha, or more preferably 0.01 to 0.5 kg of the polymorph/ha are applied.

The compositions of the invention containing sulfentrazone-1 are preferably formulated in various ways using formulation components, such as carriers, solvents and surface-active substances, for example, as described hereinafter.

The formulated compositions can be in various physical forms. For compositions containing sulfentrazone-1, these can be e.g. in the form of dusting powders, gels, wettable powders, water-dispersible granules, water-dispersible tablets, effervescent pellets, aqueous dispersions, oily dispersions, suspo-emulsions, capsule suspensions, suspension concentrates, emulsifiable granules, impregnated polymer films or in other forms known e.g. from the Manual on Development and Use of FAO Specifications for Plant Protection Products, 5th Edition, 1999. The formulated compositions can be in the form of concentrates which are diluted prior to use, although ready-to-use formulations can also be made. The dilutions can be made, for example, with water, liquid fertilizers, micronutrients, biological organisms, oil or solvents. Preferably, the formulated compositions are those wherein the sulfentrazone is maintained substantially as sulfentrazone-1 (i.e. sulfentrazone-1 is not dissolved or converted to other polymorphic forms or amorphous solids). However, in some embodiments, other formulations may be contemplated wherein the high-purity sulfentrazone-1 is used to prepare the formulation, resulting in, for example, improved environmental impact compared to formulations previously prepared using lower-purity sulfentrazone, such as Form 2 sulfentrazone. In particular, sulfentrazone-1 may be used to prepare formulations substantially free of aromatic solvents such as toluene.

The formulated compositions can be prepared e.g. by mixing sulfentrazone-1 with the formulation components to obtain compositions in the form of finely divided solids, granules or dispersions. The active ingredients can also be formulated with other components, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules usually have a diameter of from 0.1 to 500 microns. Typically, they will contain active ingredients in an amount of about from 25 to 95% by weight of the capsule weight. The active ingredients can be in the form of a monolithic solid or in the form of fine particles in solid or liquid dispersion. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other known polymers. Alternatively, very fine microcapsules can be formed in which the active ingredient is contained in the form of finely divided particles in a solid matrix of base substance, but the microcapsules are not themselves encapsulated.

The formulation components that are suitable for the preparation of compositions according to the invention are known per se. Liquid carriers include water, petroleum ether, vegetable oils, acid anhydrides, amyl acetate, butylene carbonate, cyclohexane, cyclohexanol, diacetone alcohol, 1,2-dichloropropane, diethanolamine, diethylene glycol, diethylene glycol abietate, diethylene glycol butyl ether, diethylene glycol ethyl ether, diethylene glycol methyl ether, 1,4-dioxane, dipropylene glycol, dipropylene glycol methyl ether, dipropylene glycol dibenzoate, diproxitol, alkylpyrrolidone, 2-ethylhexanol, ethylene carbonate, 1,1,1-trichloroethane, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isobornyl acetate, isooctane, isophorone, isopropyl myristate, lactic acid, laurylamine, mesityl oxide, methoxypropanol, methyl laurate, methyl octanoate, methyl oleate, methylene chloride, n-hexane, n-octylamine, octadecanoic acid, octylamine acetate, oleic acid, oleylamine, polyethylene glycol (PEG), propionic acid, propyl lactate, propylene carbonate, propylene glycol, propylene glycol methyl ether, triethyl phosphate, triethylene glycol, xylenesulfonic acid, paraffin, mineral oil, trichloroethylene, perchloroethylene, alcohols of higher molecular weight, such as amyl alcohol, tetrahydrofurfuryl alcohol, hexanol, octanol, N-methyl-2-pyrrolidone and the like. Aromatic solvents are generally not preferred as carriers. Preferably, liquid carriers are such that sulfentrazone-1 remains essentially unchanged in the herbicidal composition until after it is applied to the locus of control. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances may advantageously be used in the formulations, especially in those formulations designed to be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 2013.

Further components that can usually be used in such formulations include crystallization inhibitors, viscosity modifiers, suspending agents, dyes, anti-oxidants, foaming agents, light absorbers, mixing auxiliaries, antifoams, complexing agents, neutralizing or pH-modifying substances and buffers, corrosion inhibitors, fragrances, wetting agents, take-up enhancers, micronutrients, plasticizers, glidants, lubricants, dispersants, thickeners such as carboxymethylcellulose or xanthan gum, antifreezes, microbicides such as o-phenylphenate, and also liquid and solid fertilizers. An example of such an adjuvant is ammonium sulphate.

The formulated compositions according to the invention may additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhone-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_{8-22}$ fatty acids, especially the methyl derivatives of $C_{12-18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000. Another preferred adjuvant is Adigor® (Syngenta AG) which is a methylated rapeseed oil-based adjuvant.

The application and action of the oil additives can be further improved by combination with surface-active substances, such as non-ionic, anionic or cationic surfactants. Examples of suitable anionic, non-ionic and cationic surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12-22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltriloxanes which are commercially available e.g. as Silwet L-77®, and perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say, without oil additives.

Furthermore, the addition of an organic solvent to the oil additive/surfactant mixture may contribute to an additional enhancement of action. The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurokem Pen-e-trate®, to be added to the spray mixture as action-enhancing agent.

The compositions and formulations of this invention can also be used in combination with other active ingredients, e.g. other herbicides, fertilizers and/or insecticides, and/or acaricides, and/or nematocides, and/or molluscicides, and/or fungicides, and/or plant growth regulators and/or safeners. Such mixtures, and the use of such mixtures to control weeds and/or undesired plant growth form yet further aspects of the invention. In another embodiment, the composition further comprises at least one other herbicide. Preferably, the mixing ratio of sulfentrazone-1 described herein and the at least one additional herbicide is from 100:1 to 1:100, or from 20:1 to 1:20, or from 5:1 to 1:5, or from 2:1 to 1:2, or about 1:1.

Formulated compositions of the invention generally comprise from 0.1 to 99% by weight, especially from 0.1 to 95% by weight, of sulfentrazone-1 and from 1 to 99.9% by weight of a formulation adjuvant which preferably includes from 0 to 25% by weight of a surface-active substance. Whereas commercial products will preferably be formulated as concentrates, the end user will normally employ dilute formulations.

i) Application as a tank mix: A liquid processed mixture sulfentrazone-1 and optionally another herbicide (reciprocal ratio of amounts between 100:1 and 1:100) may be used, the application rate of herbicide being 0.005 to 5.0 kg per hectare. Such tank mixes are applied before or after sowing.

ii) Controlled release of sulfentrazone-1: The sulfentrazone-1 is applied onto mineral carrier granules or polymerized granules (urea/formaldehyde) and dried. A coating which allows sulfentrazone-1 to be released over a certain period of time can optionally be applied (coated granules).

In particular, preferred formulations have the following compositions (%=percent by weight). "Active compound(s)" means a comprising sulfentrazone-1, optionally mixed with another herbicide.

Dusts
Active compound(s): 0.1 to 10%, preferably 0.1 to 5%
Solid carrier: 99.9% to 90%, preferably 99.9 to 99%

Suspension Concentrates
Active compound(s): 5 to 75%, preferably 10 to 50%
Water: 94 to 24%, preferably 88 to 30%
Surface-active agent: 1 to 40%, preferably 2 to 30%

Wettable Powders
Active compound(s): 0.5 to 90%, preferably 1 to 80%
Surface-active agent: 0.5 to 20%, preferably 10 to 15%
Solid carrier: 5 to 95%, preferably 15 to 90%

Granules
Active compound(s): 0.1 to 30%, preferably 0.1 to 15%
Solid carrier: 99.5 to 70%, preferably 97 to 85%

Formulation Examples for Compositions of sulfentrazone-1 (optionally with another herbicide) include the following (%=% by Weight; EO=Ethylene Oxide).

Formulation 1. Wettable Powders

|  | a) | b) | c) | d) |
|---|---|---|---|---|
| active compound(s) | 5% | 25% | 50% | 80% |
| sodium lignosulfonate | 4% | — | 3% | — |
| sodium lauryl sulphate | 2% | 3% | — | 4% |
| sodium diisobutylnaphthalene-sulfonate | — | 6% | 5% | 6% |
| octylphenol polyglycol ether (7-8 mol EO) | — | 1% | 2% | — |
| highly dispersed silicic acid | 1% | 3% | 5% | 10% |
| kaolin | 88% | 62% | 35% | — |

The active compound is mixed thoroughly with the adjuvants and the resulting mixture is thoroughly ground in a suitable mill, affording wettable powders which can be diluted with water to give suspensions of any desired concentration.

Formulation 2. Coated Granules

|  | a) | b) | c) |
|---|---|---|---|
| active compound(s) | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. $CaCO_3$ or $SiO_2$ | 98.0% | 92% | 80% |

The finely ground active compound is uniformly applied, in a mixer, to the carrier moistened with polyethylene glycol. Non-dusty coated granules are obtained in this manner.

Formulation 3. Extruded Granules

|  | a) | b) | c) | d) |
|---|---|---|---|---|
| active compound(s) | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active compound is mixed and ground with the adjuvants, and the mixture is moistened with water. The mixture is extruded and then dried in a stream of air.

Formulation 4. Dusts

|  | a) | b) | c) |
|---|---|---|---|
| active compound(s) | 0.1% | 1% | 5% |
| talcum | 39.9% | 49% | 35% |
| kaolin | 60.0% | 50% | 60% |

Ready-to-use dusts are obtained by mixing the active compound with the carriers and grinding the mixture in a suitable mill.

Formulation 5. Suspension Concentrates

|  | a) | b) | c) | d) |
|---|---|---|---|---|
| active compound(s) | 3% | 10% | 25% | 50% |
| propylene glycol | 5% | 5% | 5% | 5% |
| nonylphenol polyglycol ether (15 mol EO) | — | 1% | 2% | — |
| sodium lignosulfonate | 3% | 3% | 4% | 5% |
| thickener | 1% | 1% | 1% | 1% |
| biocide | 0.15% | 0.15% | 0.15% | 0.15% |
| antifoam agent | 0.8% | 0.8% | 0.8% | 0.8% |
| water | 87% | 79% | 62% | 38% |

The finely ground active compound is intimately mixed with the adjuvants, giving a suspension concentrate from which suspensions of any desired concentration can be obtained by dilution with water.

In some instances it may be more practical to formulate sulfentrazone-1 herbicide described herein and another herbicide individually and then to bring them together as a "tank mix" in water in the application equipment in the desired mixing ratio shortly before application.

Where a polymorph of the invention, in particular, sulfentrazone-1, is combined with at least one herbicide, any of the following herbicides may be included: acetochlor, acifluorfen, acifluorfen-sodium, aclonifen, acrolein, alachlor, alloxydim, allyl alcohol, ametryn, amicarbazone, amidosulfuron, aminocyclopyrachlor, aminopyralid, amitrole, ammonium sulfamate, anilofos, asulam, atrazine, aviglycine, azafenidin, azimsulfuron, BCPC, beflubutamid, benazolin, bencarbazone, benfluralin, benfuresate, bensulfuron, bensulfuron-methyl, bensulide, bentazone, benzfendizone, benzobicyclon, benzofenap, bicyclopyrone, bifenox, bilanafos, bispyribac, bispyribac-sodium, borax, bromacil, bromobutide, bromophenoxim, bromoxynil, butachlor, butafenacil, butamifos, butralin, butroxydim, butylate, cacodylic acid, calcium chlorate, cafenstrole, carbetamide, CDEA, CEPC, chlorflurenol, chlorflurenol-methyl, chloridazon, chlorimuron, chlorimuron-ethyl, chloroacetic acid, chlorotoluron, chlorpropham, chlorsulfuron, chlorthal, chlorthal-dimethyl, cinidon-ethyl, cinmethylin, cinosulfuron, cisanilide, clethodim, clodinafop, clodinafop-propargyl, clomazone, clomeprop, clopyralid, cloransulam, cloransulam-methyl, CMA, 4-CPB, CPMF, 4-CPP, CPPC, cresol, cumyluron, cyanamide, cyanazine, cycloate, cyclosulfamuron, cycloxydim, cyhalofop, cyhalofop-butyl, 2,4-D, 3,4-DA, daimuron, dalapon, dazomet, 2,4D EHE, 2,4-DB, 3,4-DB, 2,4-DEB, desmedipham, desmetryn, dicamba, dichlobenil, dichlorprop, dichlorprop-P, diclofop, diclofop-methyl, diclosulam, difenzoquat, difenzoquat metilsulfate, diflufenican, diflufenzopyr, dimefuron, dimepiperate, dimethachlor, dimethametryn, dimethenamid, dimethenamid-P, dimethipin, dimethylarsinic acid, dinitramine, dinoterb, diphenamid, dipropetryn, diquat, diquat dibromide, dithiopyr, diuron, DNOC, 3,4-DP, DSMA, EBEP, endothal, EPTC, esprocarb, ethalfluralin, ethametsulfuron, ethametsulfuron-methyl, ethephon, ethofumesate, ethoxyfen, ethoxysulfuron, etobenzanid, fenoxaprop, fenoxaprop-P, fenoxaprop-ethyl, fenoxaprop-P-ethyl, fenoxasulfone, fentrazamide, ferrous sulfate, flamprop-M, flazasulfuron, florasulam, fluazifop, fluazifop-butyl, fluazifop-P, fluazifop-P-butyl, fluazolate, flucarbazone, flucarbazone-sodium, flucetosulfuron, fluchloralin, flufenacet, flufenpyr, flufenpyr-ethyl, flumetralin, flumetsulam, flumiclorac, flumiclorac-pentyl, flumioxazin, flumipropin, fluometuron, fluoroglycofen, fluoroglycofen-ethyl, fluoxaprop, flupoxam, flupropacil, flupropanate, flupyrsulfuron, flupyrsulfuron-methyl-sodium, flurenol, fluridone, fluorochloridone, fluroxypyr, flurtamone, fluthiacet, fluthiacet-methyl, fomesafen, foramsulfuron, fosamine, glufosinate, glufosinate-ammonium, glyphosate, halosulfuron, halosulfuron-methyl, haloxyfop, haloxyfop-P, HC-252, hexazinone, imazamethabenz, imazamethabenz-methyl, imazamox, imazapic, imazapyr, imazaquin, imazethapyr, imazosulfuron, indanofan, indaziflam, iodomethane, iodosulfuron, iodosulfuron-methyl-sodium, ioxynil, ipfencarbazone, isoproturon, isouron, isoxaben, isoxachlortole, isoxaflutole, isoxapyrifop, karbutilate, lactofen, lenacil, linuron, MAA, MAMA, MCPA, MCPA-thioethyl, MCPB, mecoprop, mecoprop-P, mefenacet, mefluidide, mesosulfuron, mesosulfuron-methyl, mesotrione, metam, metamifop, metamitron, metazachlor, metazosulfuron, methabenzthiazuron, methazole, methylarsonic acid, methyldymron, methyl isothiocyanate, metobenzuron, metobromuron, metolachlor, S-metolachlor, metosulam, metoxuron, metribuzin, metsulfuron, metsulfuron-methyl, MK-616, molinate, monolinuron, monosulfuron, monosulfuron-ester, MSMA, naproanilide, napropamide, naptalam, NDA-402989, neburon, nicosulfuron, nipyraclofen, n-methyl glyphosate, nonanoic acid, norflurazon, oleic acid (fatty acids), orbencarb, orthosulfamuron, oryzalin, oxadiargyl, oxadiazon, oxasulfuron, oxaziclomefone, oxyfluorfen, paraquat, paraquat dichloride, pebulate, pendimethalin, penoxsulam, pentachlorophenol, pentanochlor, pentoxazone, pethoxamid, petrolium oils, phenmedipham, phenmedipham-ethyl, picloram, picolinafen, pinoxaden, piperophos, potassium arsenite, potassium azide, pretilachlor, primisulfuron, primisulfuron-methyl, prodiamine, profluazol, profoxydim, prohexadione-calcium, prometon, prometryn, propachlor, propanil, propaquizafop, propazine, propham, propisochlor, propoxycarbazone, propoxycarbazone-sodium, propyzamide, prosulfocarb, prosulfuron, pyraclonil, pyraflufen, pyraflufen-ethyl, pyrasulfotole, pyrazolynate, pyrazosulfuron, pyrazosulfuron-ethyl, pyrazoxyfen, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxulam, quinclorac, quinmerac, quinoclamine, quizalofop, quizalofop-P, quizalofop-ethyl, quizalofop-P-ethyl, rimsulfuron, saflufenacil, sethoxydim, siduron, simazine, simetryn, SMA, sodium arsenite, sodium azide, sodium chlorate, sulcotrione, sulfometuron, sulfometuron-methyl, sulfosate, sulfosulfuron, sulfuric acid, tar oils, 2,3,6-TBA, TCA, TCA-sodium, tebutam, tebuthiuron, tefuryltrione, sulfentrazone, tepraloxydim, terbacil, terbumeton, terbuthylazine, terbutryn, thenylchlor, thiazafluoron, thiazopyr, thifensulfuron, thiencarbazone, thifensulfuron-methyl, thiobencarb, tiocarbazil, topramezone, tralkoxydim, triafamone, tri-allate, triasulfuron, triaziflam, tribenuron, tribenuron-methyl, tricamba, triclopyr, trietazine, trifloxysulfuron, trifloxysulfuron-sodium, trifluralin, triflusulfuron, triflusulfuron-methyl, trifop, trifop-methyl, trihydroxytriazine, trinexapac-ethyl, tritosulfuron, [3-[2-chloro-4-fluoro-5-(1-methyl-6-trifluoromethyl-2,4-dioxo-1,2,3,4-tet-rahydropyrimidin-3-yl)phenoxy]-2-pyridyloxyl]acetic acid ethyl ester (CAS RN 353292-31-6), 4-amino-3-chloro-6-(4-chloro-2-fluoro-3-methoxyphenyl)-2-pyridinecarboxylic acid (CAS RN 943832-60-8) and 4-hydroxy-3-[[2-(3-methoxypropyl)-6-(difluoromethyl)-3-pyridinyl]carbonyl-]-bicyclo[3.2.1]oct-3-en-2-one.

Particularly preferred combinations are sulfentrazone-1 and glyphosate, metribuzin, s-metalochlor, imazethepyr, chlorsulfuron, chlorimuron-ethyl, chloransulam-methyl or fluthiacet-ethyl, and more preferably metribuzin, s-metalochlor, imazethepyr, chlorimuron-ethyl or chloransulam-methyl.

While compositions comprising sulfentrazone-1 and another herbicide are explicitly disclosed above, the skilled man will appreciate that the invention extends to three-way, and further multiple combinations comprising the above two-way mixtures. Even if not explicitly stated above, the mixing partners may also be in the form of any suitable agrochemically acceptable ester or salt, as mentioned e.g. in The Pesticide Manual, Thirteenth Edition, British Crop Protection Council, 2003.

Aspects and embodiments of the invention will now be illustrated in more detail by way of the following examples.

EXAMPLES

Preparation of Polymorphs

Sulfentrazone (formula (I)) can generally be prepared as described in U.S. Pat. No. 7,169,952.

The following procedure was taken from U.S. Pat. No. 7,169,952 and is typical of the procedures used herein to prepare technical (Form 2) sulfentrazone, with possible variations related to processing conditions such as batch size, time, temperature and the like:

This example illustrates one protocol for the preparation of N-2,4-dichloro-5-4-(difluoromethyl)-4,5-dihydro-3-methyl-5-oxo-1H-1,2,4-triazol-1-yl)phenyl-methane-sulfonamide using DMF as the catalyst.

Under a nitrogen atmosphere, a 50-gallon glass lined reactor is charged with 262 pounds of a 16 wt % 1-(5-amino-2,4-dichlorophenyl)-4,5-dihydro-4-difluoromethyl 3-methyl-1,2,4-triazol-5(1H)-one in toluene solution. The solution is stirred and heated to about 105-115° C. During the heating-up period, the nitrogen atmosphere is discontinued and the reaction vessel is sealed under a vacuum of about 750-780 mm Hg. Once at the prescribed temperature, the toluene is removed at a rate to maintain the reaction temperature at about 110-120° C. and the reaction vessel pressure at 750-780 mm Hg, to yield a 50 wt % solution of 1-(5-amino-2,4-dichlorophenyl)-4,5dihydro-4-difluoromethyl-3-methyl-1,2,4-triazol-5(1H)-one (0.126 lb-mole; 1.0 equiv.—17.69 Kg) in toluene. The reaction vessel is cooled to about 85-92° C. and 168 grams (0.005 lb-moles; 0.04 equiv. 0.37 pound) of DMF is added. Methanesulfonyl chloride, 23.7 pounds (0.207 lb-mole; 1.64 equiv.-10.75 Kg), is added at a rate to maintain the reaction mixture temperature between 85-92 C. The reaction mixture temperature is then slowly brought to 140-145° C. while the reaction vessel pressure is maintained at 14-17 psig, at a rate of about 10° C. per hour. During the heating to 140-145° C., any hydrogen chloride gas that evolved is vented off. The reaction mixture is stirred at 140-145° C. for eight hours. During the eight-hour heating period, the reaction mixture is analyzed by GC every hour to determine the conversion of starting material to product. The reaction vessel is then cooled to about 83-87° C. and then vented to atmospheric pressure during a 15-minute period. Once at atmospheric pressure, 230 pounds of fresh toluene is added. The resulting solution is stirred for 30 minutes and then transferred to a separate 50-gallon glass lined reactor previously charged with 275-285 pounds of water and heated to 80-83° C. The resulting mixture is stirred at 80-83° C. for 25-35 minutes and then allowed to settle for about 25-35 minutes. The organic layer is separated from the aqueous layer and an additional 275-285 pounds of water added. After a repeat of the previously described stirring and settling, the organic layer is separated from the aqueous layer and then cooled to 20° C. during an eight hour period at a rate of 5° C./hour for the first four hours and then at a rate of 10° C./hour for the last four hours. In order to facilitate crystallization, 0.5 pound of technical N-2,4-dichloro-5-4-(difluoromethyl)-4,5-dihydro-3-methyl-5-oxo-1H-1,2,4-triazol-1-yl)phenyl-methanesulfonamide is added at 70-75° C. during the eight hour cool down period. Once at the end temperature, the organic layer is transferred into an appropriate centrifuge, where it is spun for 30 minutes to remove the mother liquor. The mother liquor is charged back into the reaction vessel, where it is stirred for 10 minutes to remove any remaining product. The mother liquor is then transferred into the centrifuge, where it is spun as previously described. The filter cake is washed with 50 pounds of fresh toluene charged directly into the centrifuge. The mixture is spun for 30 minutes to remove the toluene wash. The mother liquor and toluene wash are collected in the same receiver for reclamation of any dissolved product. The filter cake is removed from the centrifuge and dried at 80° C./30 mm Hg for eight hours, yielding N-2,4-dichloro-5-4-(difluoromethyl)-4,5-dihydro-3-methyl-5-oxo-1H-1,2,4-triazol-1-yl) phenylmethane-sulfonamide.

Analysis of technical material obtained according to the general procedure described above indicates that technical sulfentrazone contains 4.8 to 5.0 weight % toluene that is entrapped in the solid form even after crystallization from toluene. The technical material obtained as described was characterized as sulfentrazone of polymorphic Form 2, described herein.

Samples of commercially available sulfentrazone, obtained either as technical material or in herbicidal formulations, have been analyzed and determined to comprise Form 2 sulfentrazone but not the polymorphic form sulfentrazone-1 of the present invention.

Preparation of Sulfentrazone-1 by Recrystallization from 2-propanol

Sulfentrazone technical material (Form 2) (204 g, 0.53 M) was charged to a 2 liter jacketed resin kettle equipped with mechanical stirring and a circulating heating bath to control the temperature. 2-Propanol was also charged (688 g, 870 ml) to the resin kettle and the slurry was heated to 85° C. at which point a clear solution was present in the kettle. The solution was cooled slowly from about 85° C. to about 5° C. over a period of 4 hours. Precipitation of sulfentrazone-1 began when the batch temperature reached 59° C. After holding the temperature at 5° C. for 1 hour with gentle mixing, the slurry was vacuum filtered using a sintered glass funnel (1000 ml, ASTM Coarse 40-60 µm) and suctioned until dry (approx. 30 min). The crystals were transferred to a crystallizing dish and placed in a vacuum oven set at 50° C., 50 mmHg pressure and dried to constant weight.

2. Analysis of Polymorphs

After preparation by the methods detailed above, the samples were subjected to analysis by powder X-ray diffraction (XRD), Fourier Transform Infrared Spectroscopy (FTIR) and/or Differential Scanning Calorimetry (DSC) as described herein below.

Powder X-ray diffraction analysis of solid material was carried out using a Philips PW1830 diffractometer system operating at 45 kV and 35 mA. Samples were backfilled into the x-ray sample holders to allow random material orientation. X-ray diffraction signals were collected from 0° to 40° 2-theta. The diffraction patterns are shown in FIGS. 1, 2 and 3. Tables 1 and 2 show peak lists for sulfentrazone-1 and Form 2 respectively.

TABLE 1

XRD Diffraction Pattern Peak List for sulfentrazone-1

| 2-Theta | d(A) | BG | Height | I % | Area | I % | FWHM |
|---|---|---|---|---|---|---|---|
| 10.081 | 8.7675 | 177 | 853 | 28.5 | 12276 | 31.5 | 0.230 |
| 12.496 | 7.0774 | 141 | 567 | 19.0 | 7133 | 18.3 | 0.201 |
| 15.961 | 5.5481 | 213 | 2991 | 100.0 | 38998 | 100.0 | 0.209 |
| 16.278 | 5.4408 | 172 | 722 | 24.1 | 6819 | 17.5 | 0.151 |
| 17.160 | 5.1632 | 172 | 1755 | 58.7 | 24322 | 62.4 | 0.222 |
| 17.598 | 5.0355 | 113 | 502 | 16.8 | 6089 | 15.6 | 0.194 |
| 18.780 | 4.7211 | 119 | 150 | 5.0 | 1646 | 4.2 | 0.176 |
| 20.420 | 4.3455 | 95 | 367 | 12.3 | 5347 | 13.7 | 0.233 |
| 21.579 | 4.1147 | 114 | 327 | 10.9 | 4579 | 11.7 | 0.224 |
| 22.443 | 3.9581 | 101 | 311 | 10.4 | 4347 | 11.1 | 0.224 |
| 24.019 | 3.7019 | 159 | 158 | 5.3 | 1553 | 4.0 | 0.157 |
| 24.801 | 3.5870 | 179 | 1011 | 33.8 | 13612 | 34.9 | 0.215 |
| 25.217 | 3.5287 | 160 | 421 | 14.1 | 5162 | 13.2 | 0.196 |
| 25.919 | 3.4347 | 154 | 506 | 16.9 | 5599 | 14.4 | 0.177 |
| 26.658 | 3.3412 | 137 | 228 | 7.6 | 2917 | 7.5 | 0.205 |
| 28.919 | 3.0849 | 120 | 252 | 8.4 | 3938 | 10.1 | 0.250 |
| 29.523 | 3.0231 | 98 | 184 | 6.2 | 1884 | 4.8 | 0.164 |
| 30.857 | 2.8954 | 110 | 447 | 14.9 | 7259 | 18.6 | 0.260 |
| 32.461 | 2.7559 | 91 | 333 | 11.1 | 7592 | 19.5 | 0.365 |
| 32.979 | 2.7138 | 140 | 280 | 9.4 | 3593 | 9.2 | 0.205 |
| 33.723 | 2.6556 | 121 | 469 | 15.7 | 6827 | 17.5 | 0.233 |
| 34.782 | 2.5772 | 81 | 115 | 3.8 | 1257 | 3.2 | 0.175 |
| 36.216 | 2.4783 | 101 | 84 | 2.8 | 766 | 2.0 | 0.146 |
| 37.122 | 2.4199 | 100 | 66 | 2.2 | 499 | 1.3 | 0.121 |
| 37.738 | 2.3818 | 100 | 337 | 11.3 | 3515 | 9.0 | 0.167 |

TABLE 2

XRD Diffraction Pattern Peak List for Form 2

| 2-Theta | d(A) | BG | Height | I % | Area | I % | FWHM |
|---|---|---|---|---|---|---|---|
| 6.423 | 13.7502 | 4446 | 2576 | 52.3 | 18427 | 24.4 | 0.114 |
| 6.900 | 12.7993 | 2213 | 4927 | 100.0 | 75569 | 100.0 | 0.245 |
| 11.380 | 7.7688 | 184 | 224 | 4.5 | 2063 | 2.7 | 0.147 |
| 12.199 | 7.2496 | 202 | 1545 | 31.4 | 14702 | 19.5 | 0.152 |
| 13.760 | 6.4301 | 150 | 384 | 7.8 | 3233 | 4.3 | 0.135 |
| 15.383 | 5.7552 | 125 | 174 | 3.5 | 1489 | 2.0 | 0.137 |
| 17.117 | 5.1759 | 237 | 2057 | 41.7 | 18106 | 24.0 | 0.141 |
| 17.680 | 5.0125 | 201 | 333 | 6.8 | 2176 | 2.9 | 0.105 |
| 18.597 | 4.7671 | 211 | 1961 | 39.8 | 17835 | 23.6 | 0.146 |
| 19.199 | 4.6191 | 194 | 761 | 15.4 | 5910 | 7.8 | 0.124 |
| 20.038 | 4.4275 | 154 | 647 | 13.1 | 5605 | 7.4 | 0.139 |
| 20.539 | 4.3206 | 152 | 236 | 4.8 | 1804 | 2.4 | 0.122 |
| 21.042 | 4.2186 | 144 | 173 | 3.5 | 1337 | 1.8 | 0.124 |
| 21.798 | 4.0738 | 142 | 503 | 10.2 | 7111 | 9.4 | 0.226 |
| 22.700 | 3.9141 | 145 | 557 | 11.3 | 7384 | 9.8 | 0.212 |
| 24.442 | 3.6388 | 152 | 545 | 11.1 | 9175 | 12.1 | 0.269 |
| 24.698 | 3.6018 | 191 | 721 | 14.6 | 7408 | 9.8 | 0.164 |
| 25.281 | 3.5200 | 175 | 138 | 2.8 | 610 | 0.8 | 0.071 |
| 26.024 | 3.4211 | 174 | 218 | 4.4 | 2322 | 3.1 | 0.170 |
| 26.323 | 3.3829 | 167 | 217 | 4.4 | 2142 | 2.8 | 0.158 |
| 26.800 | 3.3238 | 152 | 272 | 5.5 | 2201 | 2.9 | 0.129 |
| 27.419 | 3.2502 | 176 | 348 | 7.1 | 3453 | 4.6 | 0.159 |
| 27.657 | 3.2227 | 189 | 331 | 6.7 | 2653 | 3.5 | 0.128 |
| 28.002 | 3.1838 | 208 | 123 | 2.5 | 642 | 0.8 | 0.084 |
| 28.617 | 3.1167 | 244 | 585 | 11.9 | 8014 | 10.6 | 0.219 |
| 29.059 | 3.0703 | 206 | 647 | 13.1 | 5431 | 7.2 | 0.134 |
| 29.596 | 3.0158 | 136 | 95 | 1.9 | 389 | 0.5 | 0.066 |
| 30.722 | 2.9078 | 158 | 203 | 4.1 | 1918 | 2.5 | 0.151 |
| 31.302 | 2.8552 | 145 | 239 | 4.9 | 3050 | 4.0 | 0.204 |
| 32.280 | 2.7709 | 117 | 435 | 8.8 | 6560 | 8.7 | 0.241 |
| 34.499 | 2.5976 | 138 | 462 | 9.4 | 4881 | 6.5 | 0.169 |
| 36.161 | 2.4819 | 114 | 117 | 2.4 | 1425 | 1.9 | 0.195 |
| 39.739 | 2.2663 | 97 | 179 | 3.6 | 2255 | 3.0 | 0.202 |

Differential Scanning calorimetry (DSC) was carried out using a Perkin-Elmer DSC instrument, model DSC4000, with a range of −10° C. to +445° C. A sample loading of about 3 mg to about 8 mg was used and heated from a low temperature of about 23° C. to a high temperature of 140° C., 150° C. or 200° C. at a rate of 2° C./minute. The DSC thermograms are shown in FIGS. 4 and 5.

FTIR spectra were obtained using a Bomem MB-102 FTIR Spectrophotometer equipped with a DuraSamplIR ATR accessory, with resolution at 4 cm$^{-1}$. FTIR spectra are shown in FIGS. 6, 7 and 8.

3. Formulation Examples

Sulfentrazone-1 obtained as described above was formulated as a suspension concentrate and as a wettable powder.

3a. Formulation of Sulfentrazone-1 as a Suspension Concentrate

Formulation Example 1

| Component | Description | Function | Amount | % |
|---|---|---|---|---|
| sulfentrazone-1 | | Active Ingredient | 20.5 g | 42.2 |
| Water | | Diluent | 22.5 | 46.50 |
| Tergitol ™ XD | alkyl EO/PO copolymer | nonionic surfactant | 1.0 | 2.0 |
| Tergitol ™ XH | alkyl EO/PO copolymer | nonionic surfactant | 1.0 | 2.0 |
| Dextrol ™ OC-180 | potassium salt of an ethoxylated aliphatic alcohol phosphate ester | surfactant | 0.5 | 1.03 |
| Propylene glycol | | solvent | 2.92 | 6.0 |
| Kelzan ® M | Xantham gum | thickener | 0.060 | 0.12 |
| Proxel ® GXL | aqueous solution of 1,2-benzisothiazolin-3-one | microbiostat | 0.072 | 0.15 |

Water was mixed with Tergitol™ XD and Tergitol™ XH until they dissolved completely. Dextrol™ OC-180 added. The mixture was transferred to an attritor mill and sulfentrazone-1 was added. The slurry was milled using 0.5 mm stainless steel beads until the particle size was reduced to 13μ d90. The milled slurry was separated from the milling media and Kelzan® M and Proxel® GXL slurried in propylene glycol were added to the mixture.

3b. Formulation of Sulfentrazone-1 as a Wettable Powder

Formulation Example 2

| Component | Description | Function | % |
|---|---|---|---|
| Sulfentrazone-1 | | Active Ingredient | 82.42 |
| Polyfon F | Sodium lignosulfonate | surfactant | 10 |
| Supragil ® WP | Dialkyl Naphthalene Sulphonate Sodium Salt | Wetting agent | 4 |
| Polyfon H | Sodium lignosulfonate | surfactant | 2 |
| Attaclay LVM | Attapulgite Clay | diluent | 1.58 |

Materials were blended, then milled using an air mill to reduce the particle size to less than 15 microns d90. The composition was not granulated, but it would be expected to be equivalent to a water dispersible granule formulation once suspended in water.

3b. Formulation of the Polymorph of Form 2

Formulation Comparative Example C1

Polymorph Form 2 was prepared as a wettable powder and then extruded into water-dispersible granules. This formulation is commercially available under the tradename Authority® 75DF, available from FMC.

4. Herbicidal Testing of Formulations

The formulations were tested for their pre-emergent herbicidal activity and the results are summarized in Table 3. The values reported in Table 3 are the averages of 4 replicates of each sample at the rates and on the plant species indicated.

TABLE 3

| | Rate | Crop Injury | | Weed Control | |
|---|---|---|---|---|---|
| | (g ai/ha) | Soybean | Sunflower | Redroot Pigweed | |
| | | | Untreated Control | | |
| | | 0 | 0 | 0 | |
| | | | Treatment Example | | |
| | 0 | 1 | C1 | 1 | C1 | 1 | C1 |
| 7 Days after Treatment | 210 | 0 | 0 | 21 | 26 | 100 | 100 |
| | 105 | 0 | 0 | 10 | 10 | 100 | 99 |
| | 52.5 | 0 | 0 | 21 | 7 | 100 | 81 |
| | 26 | 0 | 0 | 7 | 12 | 81 | 44 |
| 14 Days after Treatment | 210 | 0 | 0 | 13 | 36 | 100 | 100 |
| | 105 | 0 | 0 | 15 | 6 | 100 | 100 |
| | 52.5 | 0 | 0 | 9 | 3 | 100 | 83 |
| | 26 | 0 | 0 | 1 | 3 | 81 | 30 |
| 21 Days after Treatment | 210 | 4 | 0 | 21 | 49 | 100 | 100 |
| | 105 | 0 | 0 | 18 | 31 | 100 | 100 |
| | 52.5 | 0 | 7 | 17 | 28 | 100 | 88 |
| | 26 | 0 | 0 | 3 | 14 | 83 | 38 |
| 28 Days after Treatment | 210 | 10 | 0 | 20 | 43 | 100 | 100 |
| | 105 | 3 | 16 | 19 | 30 | 100 | 100 |
| | 52.5 | 0 | 11 | 36 | 24 | 100 | 86 |
| | 26 | 5 | 3 | 19 | 19 | 83 | 31 |

Inspection of the pigweed control data in Table 3 shows that the formulation using technical sulfentrazone of Comparative Example C1 had a break rate (weed control fell below 100%) of about 52.5 ai g/ha, while the formulation using sulfentrazone-1 (from Example 1) had a break rate of about 26 ai g/ha. The Example 1 formulation also showed somewhat lower crop injury than Comparative Example C1, especially at 21 and 28 days after treatment.

Although the invention has been described with reference to preferred embodiments and examples thereof, the scope of the invention is not limited only to those described embodiments. As will be apparent to persons skilled in the art, modifications to the above-described invention based on what is known and conventional in the art can be made without departing from the spirit and scope of the claimed invention. To the extent and degree that the presently claimed invention can be more fully appreciated in view of prior disclosures of what is known in the art, publications cited herein are hereby incorporated by reference in their entirety for all purposes to the same extent as if each individual publication were specifically and individually indicated to be so incorporated by reference. Such incorporation is not intended to replace or modify the present description of the invention in a manner that contradicts the present description or to expand the presently claimed invention beyond the scope of what one of ordinary skill would understand to be described herein.

The invention claimed is:
1. A sulfentrazone composition comprising a crystalline polymorphic form of N-[2,4-dichloro-5-[4-(difluoromethyl)-4,5-dihydro-3-methyl-5-oxo-1H-1,2,4-triazol-1-yl]phenyl]methanesulfonamide (sulfentrazone-1), wherein the sulfentrazone 1 is obtained by a process comprising the steps: (i) obtaining a solution, suspension, or dispersion of technical grade sulfentrazone; (ii) crystallizing sulfentrazone-1 from the technical grade sulfentrazone from a polar, protic solvent; and (iii) isolating the crystallized sulfentrazone-1 to obtain the sulfentrazone composition, wherein the sulfentrazone-1 has a powder X-ray diffraction profile that comprises peaks in terms of 2-theta at 15.9±0.2°, 10.1±0.2°, 12.5±0.2°, 33.7±0.2°, and 37.7±0.2°, wherein at least 80 weight % of the sulfentrazone composition present is sulfentrazone-1, and wherein the composition is further characterized by comprising less than 2 weight % of an organic solvent.

2. The composition of claim 1 wherein sulfentrazone-1 is crystallized from the polar, protic solvent selected from the group consisting of $C_{1-4}$ alcohols, water and combinations thereof.

3. The composition of claim 2 wherein the polar, protic solvent is isopropanol.

4. The composition of claim 3 wherein the polar, protic solvent further comprises water.

5. The composition of claim 2 wherein a saturated or near-saturated solution of sulfentrazone is obtained.

6. The composition of claim 2 wherein the technical grade sulfentrazone comprises entrapped solvent, the process further comprising: (a) heating a slurry of technical grade sulfentrazone in the polar, protic solvent selected from the group consisting of C1-4 alcohols, water and combinations thereof to provide a melt; and (b) removing the entrapped solvent by azeotropic co-distillation with the polar, protic solvent prior to crystallizing sulfentrazone.

7. The composition of claim 2 wherein crystallization is promoted by seeding with crystals of sulfentrazone-1.

8. The composition of claim 1 further comprising at least one agriculturally acceptable carrier or diluent, wherein the composition is an agrochemical composition comprising a herbicidally effective amount of sulfentrazone-1.

9. The agrochemical of claim 8 wherein at least 95% of the sulfentrazone is sulfentrazone-1.

10. The agrochemical composition of claim 8 wherein the sulfentrazone-1 is characterized by having an onset of melting in the range of from about 123° C. to about 129° C.

11. The agrochemical composition of claim 8 wherein the sulfentrazone-1 is characterized by having a single endothermic peak at about 126° C.

12. The agrochemical composition of claim 8 wherein at least about 80 weight % of sulfentrazone is present as sulfentrazone-1.

13. The agrochemical composition of claim 8 wherein at least about 95 weight % of sulfentrazone is present as sulfentrazone-1.

14. The agrochemical composition of claim 8 wherein at least about 99 weight % of sulfentrazone is present as sulfentrazone-1.

15. A method for controlling undesired plant growth which comprises applying to the locus of crop and/or undesired plant where control is desired an herbicidally effective amount of the agrochemical composition of claim 8.

* * * * *